US012742156B2

(12) United States Patent
Lau et al.

(10) Patent No.: US 12,742,156 B2
(45) **Date of Patent: *Sep. 22, 2026**

(54) METHODS AND SYSTEMS FOR TRANSPORTATION AND CULTURE OF BUOYANT TISSUE

(71) Applicant: Keliomics, Inc., Portland, OR (US)

(72) Inventors: Frank Ho Pak Lau, New Orleans, LA (US); Jason Bourgeois, San Antonio, TX (US)

(73) Assignee: Keliomics, Inc., Portland, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/249,779

(22) Filed: Mar. 12, 2021

(65) Prior Publication Data

US 2021/0284969 A1 Sep. 16, 2021

Related U.S. Application Data

(60) Provisional application No. 62/988,472, filed on Mar. 12, 2020.

(51) Int. Cl.

| | |
|---|---|
| ***C12N 5/09*** | (2010.01) |
| ***A61K 45/06*** | (2006.01) |
| ***G01N 33/50*** | (2006.01) |

(52) U.S. Cl.

CPC ............ *C12N 5/0693* (2013.01); *A61K 45/06* (2013.01); *G01N 33/5011* (2013.01); *C12N 2513/00* (2013.01); *C12N 2533/70* (2013.01)

(58) Field of Classification Search

CPC .............. C12N 5/0693; C12N 2513/00; G01N 33/5011

See application file for complete search history.

(56) References Cited

U.S. PATENT DOCUMENTS

| | | | | |
|---|---|---|---|---|
| 10,344,256 | B2 | 7/2019 | Lau et al. | |
| 11,268,059 | B2 * | 3/2022 | Lau | C12M 25/06 |
| 2019/0018002 | A1 * | 1/2019 | Hirt | C12N 5/0693 |
| 2019/0382705 | A1 | 12/2019 | Lau et al. | |

FOREIGN PATENT DOCUMENTS

| | | | | |
|---|---|---|---|---|
| EP | 1 690 928 A1 | | 8/2006 | |
| WO | WO-2013182574 A1 | * | 12/2013 | A61L 27/3895 |
| WO | 2017/066471 A1 | | 4/2017 | |

OTHER PUBLICATIONS

Www.oxfordlearnersdictionaries.com/definition/english/base-on (Year: 2022).*

Lau et al (Sandwiched White Adipose Tissue: A Microphysiological System of Primary Human Adipose Tissue. Tissue Engineering: Part C, vol. 24, Jan. 2018 (Year: 2018).*

Scahill et al (A Microphysiologic Platform for Human Fat: Sandwiched White Adipose Tissue. JOVE, vol. 138, Aug. 2018 (Year: 2018).*

Cell culture dish (Year: 2023).*

Lei et al (Co-Culturing Cancer Cells and Normal Cells in a Biochip under Electrical Stimulation. 2B0io2Chip J. (2018) 12(3): 202-207). (Year: 2018).*

Yang et al (Adipose-derived stem cells from the breast. J Res Med Sci 2014; 19:112-6 (Year: 2014).*

Zhao et al (Multipotent adipose stromal cells and breast cancer development: think globally, act locally. Mol Carcinog. Nov. 2010 ; 49(11): 923-927). (Year: 2010).*

MCF-7 (Year: 1985).*

Kodack et al (Primary Patient-Derived Cancer Cells and Their Potential for Personalized Cancer Patient Care. Cell Reports 21, 3298-3309, Dec. 12, 2017 (Year: 2017).*

MDA-MB-231 (Year: 1980).*

Chang et al (Evaluation of deacetylase inhibition in metaplastic breast carcinoma using multiple derivations of preclinical models of a new patient-derived tumor. PLoS One 15(10): e0226464, Oct. 2020 (Year: 2020).*

Song et al (Integr. Biol., 2016, 8, 205-215 (Year: 2016).*

Ballester-Beltran; et al., "Dorsal and Ventral Stimuli in Cell-Material Interactions: Effect on Cell Morphology Biointerphases", 2012, vol. 7, No. 39, 10 pgs.

International Search Report and Written Opinion mailed Nov. 28, 2016, for International Patent Application No. PCT/US2016/056879 (filed Oct. 13, 2016), 12 pgs.

Lau; et al., "Sandwiched White Adipose Tissue: A Microphysiological System of Primary Human Adipose Tissue", Tissue Eng Part C Methods (Mar. 2018), 24(3):135-145.

Mai; et al., "An Evolving New Paradigm: Endothelial Cells—Conditional Innate Immune Cells", Journal of Hematology & Oncology, 2013, vol. 6, No. 61, pp. 1-13.

Sasagawa; et al., "Endothelial Colony-Forming Cells for Preparing Prevascular Three-Dimensional Cell-Dense Tissues Using Cell-Sheet Engineering", Journal of Tissue Engineering and Regenerative Medicine, 2016, vol. 10, pp. 739-747.

Scahill; et al., "A Microphysiologic Platform for Human Fat: Sandwiched White Adipose Tissue", J Vis Exp. (Aug. 15, 2018), 138(e57909), 12 pgs.

Sorrell; et al., "The Creation of an in vitro Adipose Tissue that Contains a Vascular-Adipocyte Complex", Biomaterials, 2011, vol. 32, pp. 9667-9676.

* cited by examiner

*Primary Examiner* — Emily A Cordas
*Assistant Examiner* — Matasha Dhar
(74) *Attorney, Agent, or Firm* — LEASON ELLIS LLP

(57) ABSTRACT

Apparatuses, systems, and methods are provided for culturing a buoyant target tissue using a sandwich construct. Embodiments include preparing a buoyant target tissue in a sandwich construct for shipment, and preparing a sandwich construct comprising live tumor tissue for evaluation of candidate therapies for treating the tumor. The buoyant target tissue may include various cell types including cancer cells and tumors.

7 Claims, 21 Drawing Sheets

FIG. 9B
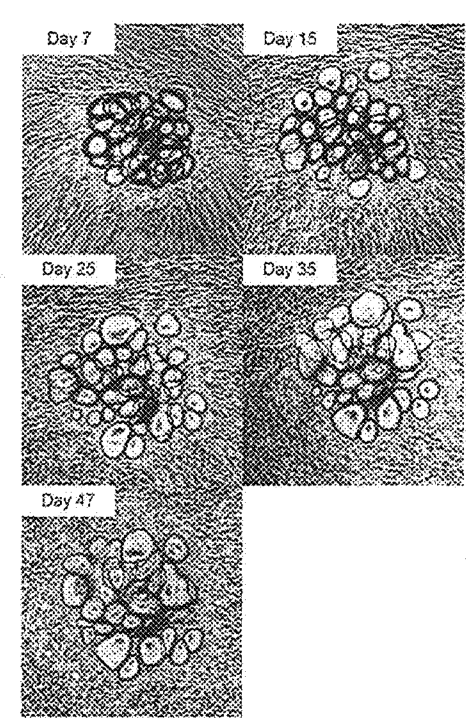
FIG. 9A
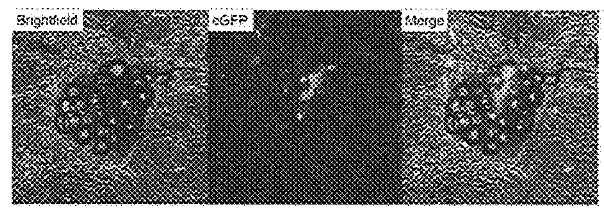
FIG. 9

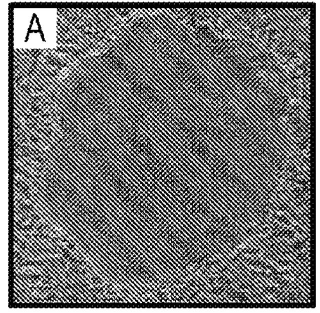
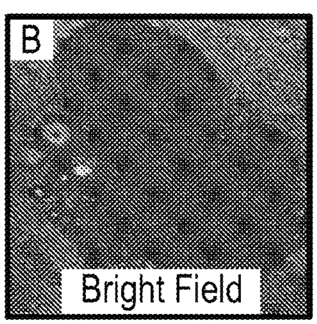
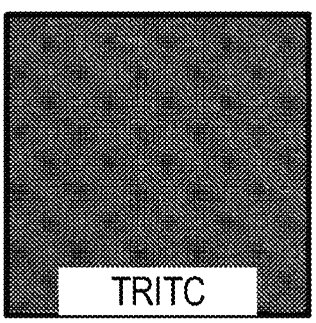
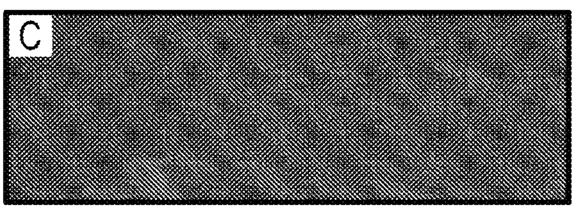
FIG. 10

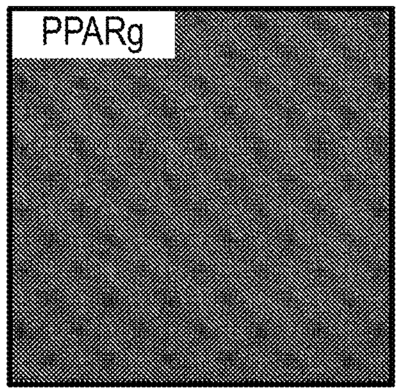
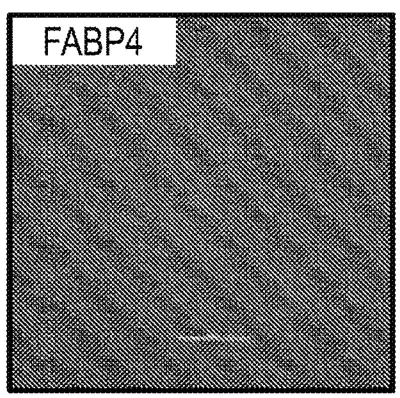
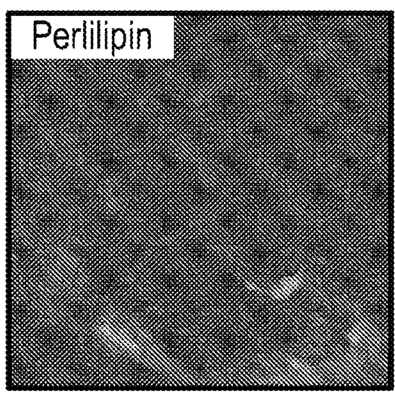
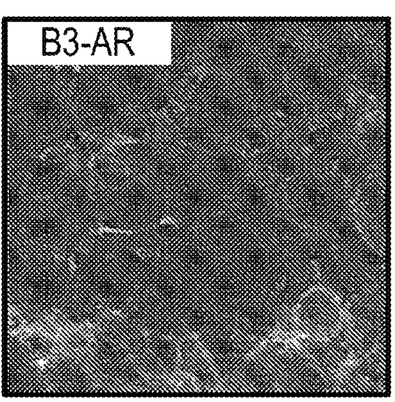
FIG. 12

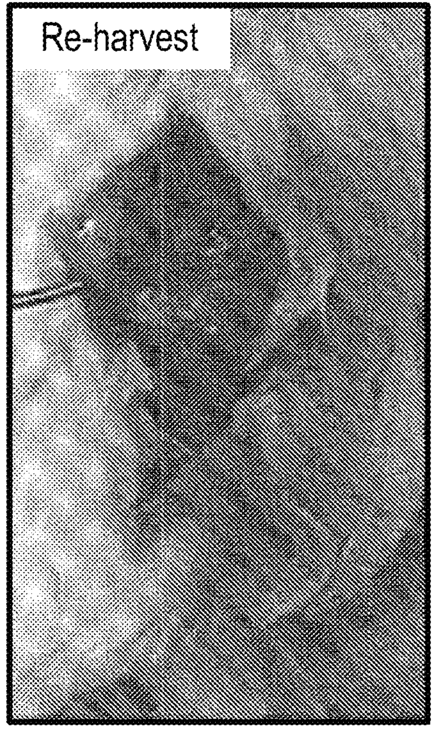
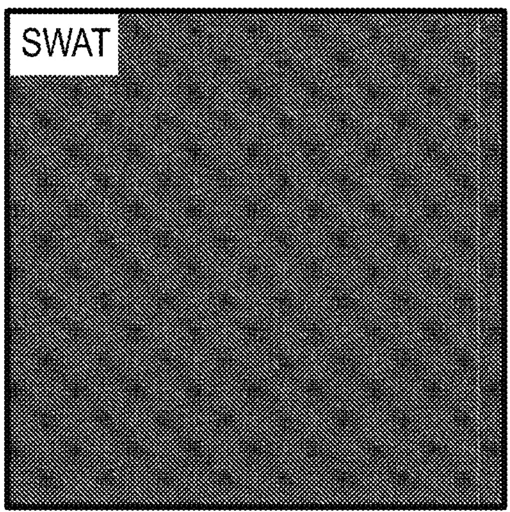
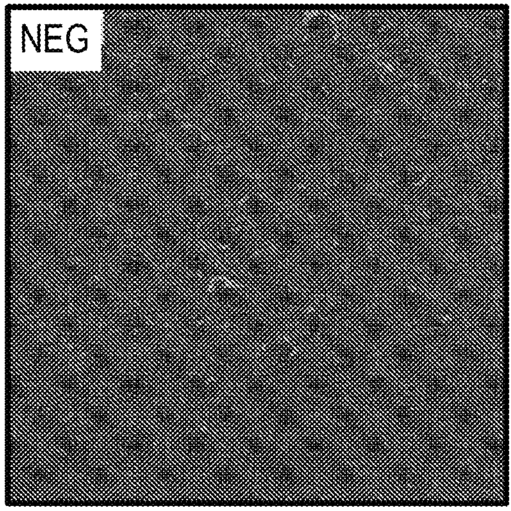
FIG. 14

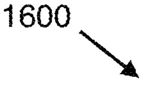
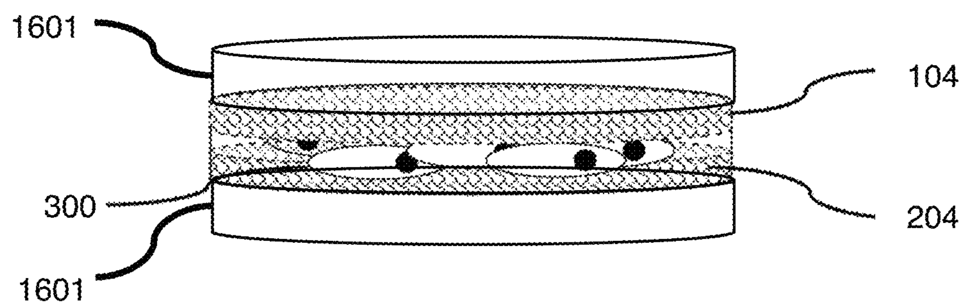
FIG. 16

1800

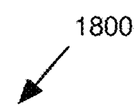

Culture a bottom layer of support cells in a first culture vessel (1802)

Culture a top layer of support cells in a second culture vessel having a warm-adhesion promoting material (e.g., pNIPAAm) (1804)

Prepare an insert device for transferring top-layer cells having a surface coated with a cool-adhesion-promoting material (e.g., gelatin) (1806)

Insert the insert device into the second culture vessel, and allow the top layer of cells to adhere to the cool-adhesion-promoting material at a moderate temperature (e.g., room temperature) (1808)

Cool the second culture vessel/insert device/top layer cells to detach cells from culture vessel while adhered to insert at a cold temperature (e.g., using ice water bath) (1810)

Transfer buoyant tissue into the first culture vessel holding the bottom layer of cells (1812)

Move the insert device, carrying top layer of cells, to the first culture vessel holding the tissue and bottom layer of cells; incubate at a warm temperature to allow top cell layer to adhere to tissue and bottom cell layer at a warm temperature; cool-adhesion-promoting material will melt and insert can be removed, leaving the sandwich construct (1814)

FIG. 18

METHODS AND SYSTEMS FOR TRANSPORTATION AND CULTURE OF BUOYANT TISSUE

CROSS-REFERENCE TO RELATED APPLICATIONS

This application claims the benefit of priority of U.S. Provisional Application No. 62/988,472, filed Mar. 12, 2020, the disclosure of which is incorporated by reference in its entirety.

FIELD

This disclosure relates generally to approaches and applications for culturing buoyant tissue.

BACKGROUND

White Adipose Tissue

White adipose tissue (WAT) is a critical organ in both health and disease. As an energy reservoir and endocrine organ, WAT regulates energy homeostasis, immunity, vascular tone, and coagulation. As the organ of disease in obesity, WAT overgrowth is a powerful risk factor for every leading cause of death, including heart disease, diabetes, stroke, and cancer. Appropriately, WAT is the subject of intense study.

However, primary WAT is difficult to maintain in vitro because adipocytes are buoyant, terminally differentiated, and prone to rupture. Approaches for overcoming these barriers have been reported since the 1970s. While these techniques were partly successful in rodent WAT, they were rarely extended to human WAT. Profound differences exist between rodent and human WAT and this enduring hurdle has slowed progress in treating human disease.

Most WAT research entirely avoids the challenges of culturing primary WAT by relying on in vitro-differentiated preadipocytes (diffAds). DiffAds have the benefit of being produced from non-buoyant stromal cells that are easily passaged using standard tissue culture methods. Although diffAds may sometimes be referred to as “adipocytes” in the scientific literature, they are not equivalent to the adipocytes as described herein. Instead, diffAds model the mechanisms of adipogenesis. For example, while white adipocytes are non-adherent, have low metabolic activity, and are unilocular, diffAds are readily adherent to typical cell culture plastics, are metabolically active, and are multilocular.

Without a well-validated in vitro model of mature human WAT, our ability to study physiology and disease is hampered. This challenge is not unique to WAT, and the need for physiologically faithful models of all human organ systems led to the creation of the National Institutes of Health (NIH) Microphysiological Systems Program. Defined as tissue-engineered, multicellular 3D organ constructs produced using human cells, microphysiological systems are expected to accelerate bench-to-bedside translation. As a broad, multi-agency effort, the NIH Microphysiological Systems Program also defined a rigorous set of benchmarks against which microphysiological systems can be evaluated.

The Tumor Microenvironment

While great strides have been made in the field of breast cancer research, there is still a need for appropriate models to accurately evaluate the role of the tumor microenvironment in breast cancer progression. Known factors that contribute to cancer progression and drug resistance have been attributed to remodeling of the tumor microenvironment. Some of these factors include cellular crosstalk, extracellular matrix (ECM) remodeling of the tumor microenvironment, and hypoxia.

The breast tumor microenvironment is home to a heterogeneous population of cells that may include adipose-derived stromal cells (ASCs), adipocytes, stromal cells, immune cells, and cancer cells. These cells coexist in a complex relationship; crosstalk between these cell types is reciprocal and drives disease progression. ASCs are recruited to the tumor microenvironment where they promote tumorigenesis through a number of ways. ASCs have immunomodulatory capabilities and have been shown to inhibit natural killer cells and cytotoxic T-lymphocytes. Additionally, ASCs can become cancer-associated fibroblasts when exposed to the secretome of triple negative breast cancer cells (MDA-MB-231 cell line) and estrogen receptor positive (ER+) breast cancer cells (MCF-7 cell line) through TGFβ1 via SMAD3. Cancer cells can also actively direct metabolic activity in stromal cells: fibroblasts and adipocytes can be directed to use catabolic pathways to fuel anabolic tumor growth by transferring lactate, ketones, glutamine, and fatty acids to cancer cells. Cancer-associated adipocytes at the tumor-stromal interface can experience de-lipidation and acquire a fibroblast-like phenotype as they undergo cancer-mediated lipolysis to release free fatty acids to the cancer cells. Additionally, adipocytes have been shown to sequester and metabolize chemotherapeutics reducing the active drug concentration in the tumor microenvironment.

Growing tumors also experience immune cell infiltration and inflammation. Macrophages are recruited by adipocytes that secrete monocyte chemoattractant protein 1 and tumor necrosis factor α (TNFα). Activated macrophages promote pro-tumorigenic remodeling such as angiogenesis. As tissues expand, homeostasis is disrupted causing resident macrophages and mast cells to release signaling molecules that recruit leukocytes from circulation to the growing tissue. In adipose tissue, macrophages are the most common type of leukocyte. Activated macrophages promote pro-tumorigenic remodeling such as angiogenesis.

As breast cancer progresses, the tumor microenvironment undergoes dramatic changes. Fibrotic remodeling of the ECM, called desmoplasia, occurs. Myofibroblasts play a major role in breast adipose tissue remodeling through the degradation of existing ECM and production of a denser, fibrillar collagen I and fibronectin rich matrix. Matrix metalloproteinases are used by the stromal cells to degrade the ECM which releases bound growth factors that activate cell growth signaling pathways and facilitate tumorigenesis. Matrix metalloproteinases are also used to degrade the basement membrane at the tumor-stroma interface and the basement membrane is replaced with fibril collagen arranged perpendicular to the tumor to facilitate invasion.

Tumor growth also creates areas of hypoxia which leads to angiogenesis, a hallmark of cancer. The metabolic burden induced by the expanding tumor depletes the microenvironment of nutrients and oxygen while polluting it with metabolic wastes that must be removed. In response to these low oxygen conditions, the transcription factor hypoxia-inducible factor 1 is expressed which triggers the release of angiogenesis inducers vascular endothelial growth factor A, placental growth factor, and angiopoietin 1. Hypoxia-inducible factor 1 can also contribute to dysregulated metabolism in expanding tumors by shifting ATP generation from oxidative phosphorylation to glycolysis. In tumor cells, this shift is referred to as the Warburg effect and can even occur under normal oxygen concentrations. Interestingly, the reverse Warburg effect was observed when cancer associated fibroblasts were found to secrete lactate and pyruvate in a paracrine exchange with tumor cells thereby allowing the tumor cells to generate energy through mitochondrial oxidative metabolism.

All of the factors discussed thus far demonstrate that the tumor microenvironment is complex and dynamic. In an attempt to develop more complex breast tumor models that recapitulate the tumor microenvironment, researchers are turning to engineered tumor microenvironments and 3D bioprinting. 3D hydrogels are an interesting option to create a more accurate tumor model. They provide a platform that is tunable by allowing researchers to choose ECM composition, alter stiffness, and control hypoxia levels. While 3D hydrogel breast tumor models allow for the integration of components that contribute to a more physiologically relevant tumor model, they often consist of only one or two ECM substrates and fail to consider the complex interplay between the cells of the tumor microenvironment. One hydrogel model addressed the single cell type issue by coculturing HepG2 human hepatocellular liver carcinoma cell line with growth arrested fibroblasts forming heterospheroids in a 3D collagen I hydrogel. The heterospheroids proved to be more drug resistant than 2D monolayer and homospheroid cell cultures. Although this heterospheroid model was an improvement from hydrogel, it still contained only collagen I and just two cell types. Microfluidics devices are more complicated models that can be used to integrate physiological phenomenon such as fluid flow, spatially controlled cocultures, and signaling gradients into cancer models. In cancer models, microfluidics devices have been used to study angiogenesis, migration, and metastasis. As powerful and complex as these engineered microsystems can be, they still lack the ability to accurately recreate the tumor microenvironment because they lack tumor-derived matrix and cancer-associated stromal cell populations. Patient-derived xenograft (PDX) models bring us even closer to a complete model by using actual breast tumors cultured in vivo, but there are some inherent issues with PDX models. Xenograft models involve cross-species implantation and must be done in immunodeficient animals which removes crosstalk between immune and other resident cells which is a key factor in tumorigenesis. Immunotherapy is a promising form of anti-cancer therapy for solid tumors, yet translation to the clinic is limited in part due to lack of an immunocompetent 3D tumor model. Cross species models are limited in informatics analysis where separation of species is required. Mouse models also lack recapitulation of human remodeling of the tumor microenvironment. Additionally, patient-derived breast tumors have a very low success rate when implanted (10-25%) with a high associated cost. The high cost to experiment with PDX models limits access to only labs that are well funded.

The need for better tumor models is further evident in the fact that only 18% of compounds in phase II and 50% of compounds in phase III clinical trials go on to successfully meet FDA approval. The development of new compounds is labor and resource intensive. Such high failure rates led the NIH to invest $70 million in the Microphysiological Systems Program with the goal of developing better models to predict efficacy and toxicology of novel compounds to improve success rates.

The lack of complexity in most of the current breast tumor models leads to a gap in our knowledge in the role that the tumor microenvironment specifically contributes to the progression of breast cancer to a more aggressive phenotype. ECM and adipose tissue are not integral components of in vitro drug studies where the gold standard is still tissue culture plastic. To fully understand the link between breast tumor microenvironment and breast cancer, a tumor model that recapitulates these interactions, crosstalk, and feedback loops between tumor microenvironment and cancer cells is required. We describe herein a novel ex vivo human breast tumor model. This model is expected to comply with NIH Microphysiological System standards. This novel breast tumor model is viable, versatile, and physiologically relevant.

The interaction between breast cancer cells and their microenvironment is a critical factor that influences the tumor biology and response to therapy. Appropriate modelling to study breast cancer for the development of new treatments requires a system that reproduces the heterogenous nature of a breast tumor and the tumor microenvironment. Current models for studying breast cancer in vitro rely on simplified systems of culturing cancer cell lines on regular tissue culture plastic, on simple collagen gels, or in 3D tumor spheroids. While these models are relatively cheap and easy to use, they do not fully recapitulate the native environment of the breast tissue. Studying breast cancer in vivo using PDX relies on immunocompromised mouse models and the human tumors are grown in a murine environment that may not accurately mimic what occurs in a human. In addition, PDX models are time consuming and expensive.

Cancer cells are very difficult to grow in vitro; the few that are routinely used (e.g., HeLa cells) are quite different from any cancer cell likely existing in a current patient. Moreover, the vast majority of primary tumor cells (e.g., a tumor isolated from a patient) cannot be grown in culture. Accordingly, even if buoyant adipose tissue such as WAT could be maintained in culture, it does not suggest that cancer cells or tumor tissue could likewise be maintained in a similar culture system. For example, if small tumor fragments are placed into standard tissue culture, the fragments most commonly undergo necrosis. While cell lines can occasionally be derived from tumor fragments, the tumor architecture is lost. This disclosure presents novel techniques and evidence that the sandwich construct culture systems described herein can be adapted to maintain cancer cells and tumor tissue—a breakthrough development.

Some cancers respond unpredictably to particular treatment regimens, and some have many possible treatment regimens to choose from. The course of chemotherapy can be influenced by interactions between the cancers and nearby tissues such as adipose tissue. For example, one category of invasive breast cancer—luminal tumors that are hormone receptor positive and HER2 negative—exhibit a variable response to neoadjuvant endocrine therapy. 30% of patients do not respond to neoadjuvant endocrine therapy alone and would benefit from a more aggressive treatment regimen. Ex vivo model systems that can model tumor/breast tissue interactions are needed to guide decisions about treatment regimens to limit experimenting on the patient, or over- and under-treating patients.

SUMMARY

Applicants have found that a sandwich construct comprising two layers of support cells sandwiching a target tissue of primary buoyant tissue and tumor tissue or cancer cells can maintain the target tissue in culture, where previously live tumor tissue has generally not been maintainable in culture. Where the target tissue comprises white adipose tissue (WAT), the sandwich construct is a sandwiched WAT (SWAT). Applicants have additionally developed a solution for transporting target tissue based on the sandwich construct.

In one aspect, a method is provided for preparing a buoyant tissue culture for transport. The method includes forming, in a container, a first layer of support cells that adheres to a surface of the container submerged in an aqueous culture medium; disposing a buoyant tissue sample adjacent to an upper surface of the formed first layer of support cells; depositing a second layer of support cells over the first layer of support cells and the tissue sample to form a sandwich construct that is submerged in the aqueous culture medium; culturing the buoyant tissue sample, wherein the tissue sample comprises a tissue explant from an individual; and disposing a layer of protective material over the sandwich construct.

In a further aspect, a method is provided for evaluating a candidate treatment for a tumor in an individual. The method includes isolating a population of healthy cells from a first sample of healthy buoyant tissue; generating a population of support cells based on the population of healthy cells; culturing the population of support cells to form two layers of support cells; preparing a target tissue based on a second sample of healthy buoyant tissue and a third sample of live tumor tissue, wherein the second and third samples are from the individual and the target tissue comprises a population of tumor tissue; assembling a sandwich construct in a culture vessel, wherein the sandwich construct comprises a bi-layer construct in which the two layers of support cells sandwich the target tissue; exposing the sandwich construct to the candidate treatment; and evaluating the change in the status of the population of tumor tissue in the target tissue in response to the candidate treatment.

BRIEF DESCRIPTION OF THE DRAWINGS

The aspects and advantages of the invention will become more apparent upon consideration of the following detailed description, taken in conjunction with the accompanying drawings, in which like reference characters refer to like parts throughout, and in which:

FIG. 9 shows microscopic images illustrating the morphologic stability of a SWAT cell culture system, according to an exemplary embodiment of the present disclosure.

FIG. 9A shows microscopic images of a SWAT culture system having a bi-layer of support cells surrounding a WAT cell cluster, according to an exemplary embodiment of the present disclosure.

FIG. 9B shows microscopic images illustrating the morphologic stability of WAT cell clusters in the SWAT cell culture system, according to an exemplary embodiment of the present disclosure.

FIG. 10 is a series of microscopic images showing the long-term stability of a WAT cell cluster in a SWAT culture system, according to an exemplary embodiment of the present disclosure.

FIG. 12 shows microscopic images indicating that SWAT cultures are translationally active and express protein associated with adipose tissue identity, according to an exemplary embodiment of the present disclosure.

FIG. 14 shows images illustrating that SWAT cultures fully engraft into immunocompromised, eGFP-labeled mice, according to an exemplary embodiment of the present disclosure.

FIG. 16 is an illustration of a means for shipping the SWAT model that is intended to avoid disruption of the placement of the buoyant tissues incorporating gelatin layers above and below the SWAT model, according to exemplary embodiments of the disclosure.

FIG. 18 is a flow chart for an exemplary process for preparing a sandwich construct for maintaining a target buoyant tissue, according to exemplary embodiments of the disclosure.

DETAILED DESCRIPTION

Figure 1A:
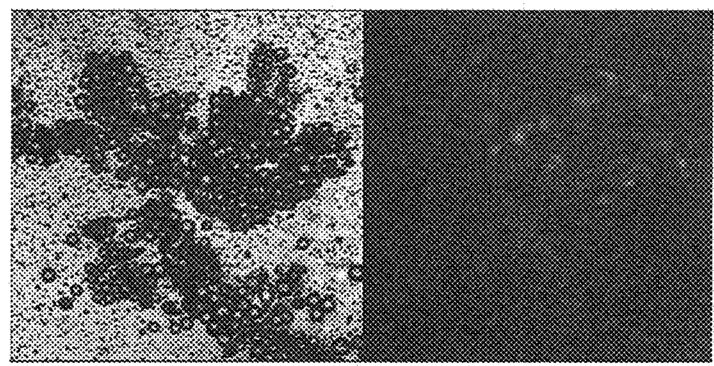
FIG. 1A shows microscopic images of human white adipose tissue (WAT) cultured in a matrix of collagen after 2 days of conventional, collagen-embedded culture.

As used herein, "white adipose tissue" (WAT) refers to a tissue primarily comprised of mature, terminally differentiated white adipocytes. Primary WAT is WAT that has been isolated from an animal such as a human, as distinguished from, e.g., a tissue that has been derived from a cell line.

As used herein, "adipocyte" refers to a mature, terminally differentiated fat cell. A primary adipocyte has been isolated from an animal. Adipocytes may be, for example, white or brown.

As used herein, a "diffAd" refers to a preadipocyte differentiated in vitro. DiffAds and adipocytes have a different expression profile.

As used herein, "support cells" are cells that can grow on and adhere to the surface of a tissue culture vessel, and that can themselves support the growth and/or maintenance of buoyant cell tissue. Support cells may include, for example, pluripotent stem cells associated with a tissue type, in vitro-differentiated stem cells such as diffAds, stromal cells such as adipose-derived stromal cells (ASC) and breast-derived stromal cells (BSC), or in-vitro-differentiated cells derived from stromal cells. ASC are adherent to many cell culture vessel surfaces, and functionally support adipose tissue by, e.g., secreting extracellular matrix proteins, growth factors, and/or cytokines that are native to a particular adipose tissue.

As used herein, a "thermoresponsive material" is a material that has two or more temperature-dependent states. For example, in a first temperature-dependent state (e.g., within a respective temperature range), the material may allow or promote cell adhesion at a surface, and in a second temperature-dependent state (e.g., outside of the respective temperature range), disrupts or inhibits cell adhesion at the surface. Thermoresponsive materials may include warm adhesion-promoting materials and cold adhesion-promoting materials. Warm adhesion-promoting materials may allow or promote cell adhesion above a threshold temperature or temperature range, and disrupt or inhibit cell adhesion at lower temperatures, e.g., by contracting or destabilizing the surface. One example of a warm adhesion-promoting material is based on poly(N-isopropylacrylamide) (pNIPAAm), which can be used to form a surface coating that allows cell adhesion at a typical mammalian body temperature, but which can disrupt cell adhesion at a cool temperature near 0° C. Cool adhesion-promoting materials generally allow or promote cell adhesion at a surface below a threshold temperature or range, e.g., below the melting point of the material, and disrupt cell adhesion at warmer temperatures, e.g., because the material has melted. Examples of cool adhesion-promoting materials include coatings or structures based on gelatins or waxes. Thermoresponsive materials may include, e.g., polymer or hydrogel coatings for one or more surfaces of a structure such as standard tissue culture plastic or another culture vessel, or may form the bulk of the structure providing a surface itself when in a stable, adhesion-promoting state.

As used herein, a breast tumor microenvironment is a heterogeneous population of cells that may include WAT, ASCs and other stromal cells, adipocytes, immune cells, and cancer cells.

As used herein, a "buoyant tissue" refers to at least one of: a tissue that may not be able to adhere directly to the surface of standard culture tissue plastic or another culture vessel; a tissue that may not be maintained if in contact with the surface of a culture vessel; or at tissue that may be buoyant in an aqueous culture medium.

Obesity is an increasingly common condition afflicting over 79 million Americans. Obesity may be associated with various diseases including: type 2 diabetes, heart disease, stroke, arthritis, and some cancers. Presently, there is a strong need for anti-obesity therapeutics approved for human intervention.

Obesity may be described as an overgrowth of white adipose tissue (WAT) in the body. In general, WAT may be considered an organ in the human body, functioning as an energy reservoir where extra calories may be stored. WAT is found throughout the human body and may be subcutaneous in origin, or originate from a variety of anatomical areas including, intra alia, the abdomen, chest, gluteus, and limbs. WAT may also be considered an endocrine organ that produces hormones to regulate multiple physiological systems, e.g., hunger/satiety, glucose metabolism, and lipid metabolism. A properly functioning WAT organ is critical. Indeed, insufficient WAT may lead to illness or death.

As an organ, WAT includes mature white adipocytes that may be described morphologically as large cells having a unilocular lipid droplet that exceeds 95% of cellular volume. The presence of this large lipid droplet renders white adipocytes buoyant. Human white adipocytes may also be considered as exceptionally fragile cells due in large part to their size. For example, human white adipocytes range in size from about 100 to about 140 μm in size, which is nine times the volume of rodent white adipocytes.

Attempts to culture primary, human white adipocytes have largely been unsuccessful. Conventional in vitro culture methodologies employ techniques such as enzymatic treatment and mechanical handling to dissociate primary WAT and isolate the white adipocytes. This treatment typically destroys or severely damages a large proportion of the white adipocytes, wherein the majority of white adipocytes undergo cell lysis within 72 hours after handling. Accordingly, research models of human WAT derived from white adipocytes do not exist.

Figure 1B:
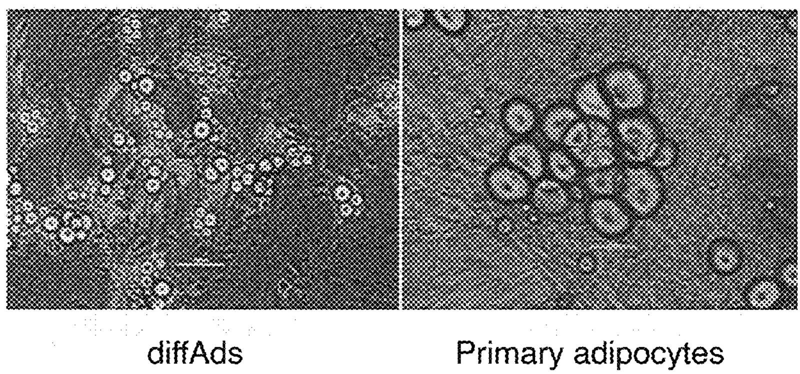
FIG. 1B shows microscopic images illustrating differences in morphology between diffAds and primary adipocytes.

Attempts to overcome the challenge associated with white adipocyte culture include embedding white adipocytes in a matrix of collagen protein. However, this technique has had limited success. FIG. 1 shows micrographs of collagen-embedded human WAT stained with propidium iodine indicating the induction of programmed cellular death, a.k.a., apoptosis, after 2 days of culture. In addition to their fragility, adipocytes are also considered terminally differentiated and mitotically inactive. Therefore, white adipocytes may not be expanded in culture without altering their differentiation state, i.e., dedifferentiating.

Unlike most other model cell types, for which stocks of cells may be frozen for long-term storage, human WAT/white adipocytes must be obtained fresh from the operating room or clinic and used immediately for each experiment. Researchers must, therefore, rely on surgically procured, human WAT as a source material, which limits the availability of WAT/white adipocytes to non-clinician researchers. In fact, researchers lacking relationships with clinicians may not have access to human WAT. Research experiments may then become tied to clinician schedules, which can be unpredictable. Further, tissue procurement may be time-consuming, and often requires travel, donning of surgical attire, and hospital approval of investigational protocols. These barriers to accessing source WAT have slowed the overall pace of scientific discovery and may deter researchers from investigating the biology of human WAT altogether.

Currently, researchers rely on models including rodent models or stromal/stem cell models chemically differentiated into adipocyte-like cells (i.e., diffAds). However, these experimental models fail to recapitulate primary, human WAT biology. For example, one of the first-identified anti-obesity pathways was controlled by beta-3 adrenoreceptors (β3-ARs). Using selective β3-AR agonists, obesity and diabetes were successfully cured in several rodent models. However, the same selective β3-AR that were successful in rodent models of obesity had little activity against human β3-ARs, resulting in multiple failed clinical trials.

Similarly, certain model cell types, e.g., stromal and stem cells, may be chemically differentiated into adipocyte-like cells (i.e., diffAds). However, diffAds only express human white adipocyte markers, including CCAAT/enhancer-binding protein alpha, lipoprotein lipase, fatty acid binding protein 4, and hormone sensitive lipase, at a reduced levels. Further, models of obesity based on diffAds fail to recapitulate white adipocyte functionality in metabolic assays measuring glycerol release, adiponectin release, and glucose uptake.

Figure 2:
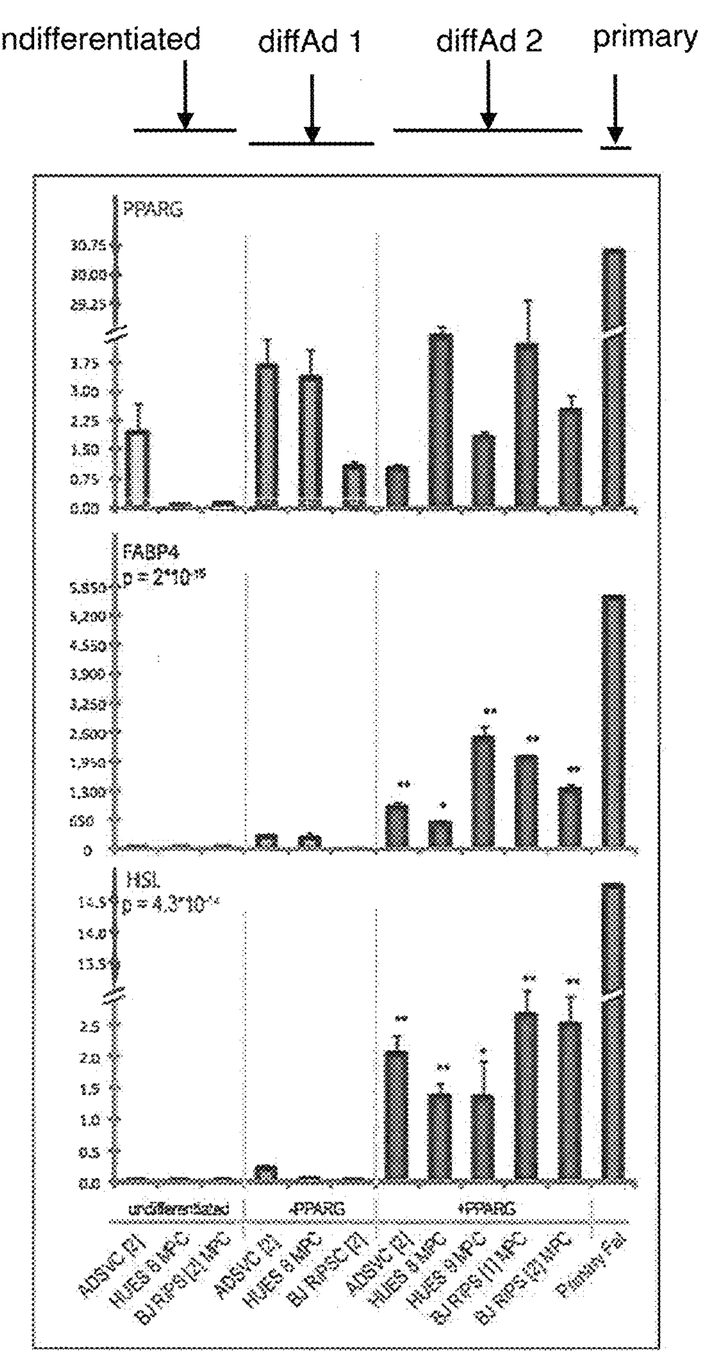
FIG. 2 is a graphical illustration comparing gene expression of adipocyte identity genes between conventional culture models and primary WAT.

Genetically, in vitro cell models do not share similar gene expression patterns with white adipocytes. FIG. 2 graphically illustrates the variation in adipocyte identity gene expression between conventional culture models and primary WAT. The "diffAd 1" bars within FIG. 2 represent the expression levels of diffAds, which are stem cells differentiated into multiloculated adipocyte-like cells using standard protocols in vitro. The "diffAd 2" bars within FIG. 2 represent the expression levels of stem cells differentiated into "adipocytes" using PPARg-expressing lentivirus constructs in vitro. The bar labeled "primary" within FIG. 2 represents the expression levels of primary adipose tissue. As shown, primary adipose tissue expresses adipocyte genes at levels 10 to 100 times greater than in vitro models. Accordingly, conventional models fail to recapitulate the gene expression levels of primary adipose tissues.

Stable, in vitro culture of primary human WAT is important because long-term viability is a proxy for cellular health. Populations of progressively dying cells produce unreliable data and misleading results. Long-term culture of WAT has persisted as an unsolved challenge because adipocytes are buoyant and prone to death. These qualities precluded the use of standard tissue culture surfaces. Attempts to embed adipocytes in extracellular matrices (ECM) preserved rodent adipocyte viability but, to our knowledge, have not been successfully extended to human WAT.

In cell sheet engineering, cell sheets are grown on and released from thermoresponsive substrates such as poly(N-isopropylacrylamide). Because the release process does not require enzymatic digestion, the ECM is preserved. In SWAT, the preserved ASC ECM serves two functions: 1) it recapitulates the native stromal environment and 2) it rapidly and powerfully bonds the ASC sheets, thus overcoming WAT buoyancy.

Unlike other adipose microphysiological systems, SWAT utilizes primary human WAT rather than diffAds or rodent adipocytes. This distinction matters because diffAds fail to recapitulate primary adipocyte physiology even under optimized conditions. For example, we previously showed that human pluripotent cells fully differentiated into diffAds express key adipocytes genes at <1% of primary WAT, even under lentiviral-driven conditions. It has been further shown that in vitro and in vivo differentiation are transcriptionally distinct, suggesting that diffAds are an incomplete model of adipogenesis. Similarly, it has long been recognized that the physiologies of rodent and human adipocytes differ in crucial aspects, such as the density of beta-3-adrenoreceptors. Because of these shortcomings, it is crucial that adipose microphysiological systems utilize primary human WAT.

For adipose biologists, SWAT offers several advantages. First, the ability to culture SWAT for weeks allows the study of slow-developing WAT phenomena such as adipocyte turnover, hypertrophy, and fibrosis. Second, the non-floating nature of SWAT allows single adipocytes to be monitored over time through previously inapplicable techniques such as time-lapse imaging. Third, the thermoresponsive substrates used are commercially available and inexpensive, thus avoiding the need for microchip fabrication expertise. Lastly, SWAT is readily generated from multiple adipose tissue depots, from both female and male subjects, from normal weight, overweight, and obese subjects, and from diabetic and non-diabetic subjects. These advantages make SWAT a low-cost and highly feasible technique that avoids the need for lengthy differentiation protocols.

One of the issues with implementing the SWAT model or other sandwich construct is that the nature of the constituent buoyant tissues makes the model sensitive to disruption during handling. This problem is magnified during shipping of the model to outside laboratories. Shipping solutions for ameliorating this disruption are described herein. These shipping solutions seek to prevent fluidic shear forces that would lift the buoyant tissues or cells as well as any other cells suspended therein (e.g. cancer cells or tumors) off the plate. In certain embodiments, the shipping solutions lower the temperature of the model to minimize the metabolic rate of the buoyant tissues or cells as well as any other cells suspended therein (e.g. cancer cells or tumors) without incurring ice crystal damage. In certain embodiments, the shipping solutions allow circulation of sufficient nutrients and facilitate gas exchange in order to prevent cell death.

In a single or multi-well plate or other appropriate culture vessel or container, a layer of gelatin may be disposed on the bottom of the well. The SWAT model as described herein may then be layered on top of this gelatin layer. A second gelatin layer is then disposed on top of the SWAT model, thus fully encapsulating the SWAT model on all sides. A biological anti-freeze (e.g. Wisconsin transplant solution) may be used to allow the model to be brought down to freezing or near freezing temperatures. A plunger system may be further employed to secure the top gelatin layer. In certain embodiments of a shipping solution, any sandwich construct may be used in place of a SWAT model. In certain embodiments, in place of layers or a coating of gelatin, an alternative protective material, such as a cold adhesion-promoting material may be used to encapsulate or sandwich the SWAT or sandwich construct.

Human Breast Tissue Model

A human breast tissue model can be made using a sandwich construct. For example, cell sheets (support cell layers) may be formed for top and bottom layers using ASCs that were previously isolated from native breast tissue using collagenase digestion and stored in liquid nitrogen. Bottom layer sheets may be cultured on tissue culture plastic dishes. Minced native breast tissue is mixed with breast cancer cells and then sandwiched between the top and bottom cells sheets. A plunger apparatus containing a layer of gelatin at one end may be used to remove the top cell sheet from the dish by chilling it on ice. The cell sheet/plunger may be placed on top of the bottom layer with the cells and/or adipose seeded on it. The dishes may be placed in the incubator to melt the gelatin and liberate the cell sheets to create the model. Human breast tissue may be a complete tissue—i.e., it may include any cell type that may naturally occur in human breast tissue. For example, in addition to adipose tissue, human breast tissue as used herein may include immune cells, and/or may include ER+ or ER− breast cancer cell lines or solid tumors.

When constructed, human breast tissue may be a complete tissue. Native breast tissue consisting of heterogeneous cell populations may be mixed with ER+ or ER− breast cancer cell lines and encapsulated in engineered ASC cell sheets. This design allows for coculture of breast cancer cell lines with stromal cells in a physiologically relevant 3D environment. The experimental design allows one to collect multiple timepoints to track intra-tumoral progression. Compatible assays include, but are not limited to, scanning electron microscopy (SEM) imaging, immunohistochemistry (IHC), immunofluorescent (IF) antibody staining, quantitative PCR (qPCR), proteomics, lipidomics, and western blot. QPCR and western blot can be used to analyze a whole sample of human breast tissue or on populations of individual cell types isolated from human breast tissue and separated using fluorescence-activated cell sorting (FACS).

Human breast ASCs and breast tissue from elective surgery can be used to make the human breast tissue model. The ASCs are normal stromal cells of the breast microenvironment that secrete extracellular matrix proteins, growth factors, and cytokines that are native to the breast tissue. The ASC cell sheets provide growth factors to keep the breast tissue healthy and serves to anchor the buoyant human breast tissue. By using ASCs derived from human breast tissue, this method ensures that the interactions that the ASCs have with the cancer cells will mimic what occurs in breast cancer in vivo; ASCs from different depots display different gene expression and ECM remodeling.

The use of fully mature adipocytes from human breast tissue is also important as adipocytes influence cancer development, drug response, and invasiveness. Previous models studying the interaction between adipocytes and cancer cells use preadipocytes that are differentiated in vitro (i.e., diffAds). Preadipocytes that are differentiated in vitro do not fully mature to the same extent as adipocytes matured in vivo. To understand how the adipocytes influence cancer progression and drug response, it is vital that we use cells that express the same genes and respond the same way as the adipocytes in native breast tissue. The culturing of primary mature breast tissue that has not been enzymatically digested allows for the ECM proteins and growth factors from the breast tissue to be retained in the human breast tissue. This model system will allow for a more accurate understanding of how the stromal environment influences tumor biology.

DESCRIPTION OF THE EMBODIMENTS

Apparatuses, methods and systems are provided for culturing tissues and cells. In exemplary, non-limiting embodiments, apparatuses, methods and systems are provided for culturing buoyant, primary, human tissue explants and cells under conditions capable of maintaining primary cell type characteristics, including morphology, gene and protein expression levels, and metabolic function, even after extended periods of time in culture.

In exemplary embodiments, apparatuses, methods, and systems for in vitro culture of buoyant tissue explants of human WAT are provided.

Embodiments of the present disclosure provide systems, methods, and apparatuses for culturing buoyant tissues and cells when added to an aqueous culture medium. Embodiments of the present disclosure provide systems, methods, and apparatuses for culturing primary, human tissue explants and cells obtained from individuals, e.g., patients. Embodiments of the present disclosure provide systems, methods, and apparatuses for culturing human tissue and cells for extended periods of time, e.g., several weeks, in a stable, differentiated state.

Embodiments of the present disclosure provide systems, methods, and apparatuses for configuring a micro-physiological, e.g., organ-on-a-chip, model system. Embodiments of the present disclosure provide for the evaluation of the effect of chemical compounds, such as pharmaceuticals, on human tissue explants and cells cultured via the systems, methods, and apparatuses disclosed herein. The present embodiment may include other cell types integrated within the buoyant tissue and cell types. This may include cancer cells and tumors including but not limited to breast cancers (e.g. Ductal carcinoma in situ (DCIS), Lobular carcinoma in situ (LCIS), ER+ breast cancers, PR+ breast cancers, Her2/neu+ breast cancers, Triple negative breast cancers, BRCA1+ breast cancers, BRCA2+ breast cancers, and Inflammatory breast cancers), colon cancers (CMS1 subtype, CMS2 subtype, CMS3 subtype, CMS4 subtype, carcinomatosis (spread throughout abdominal cavity)), Prostate cancers (Adenocarcinomas, Small cell carcinomas, Neuroendocrine tumors (other than small cell carcinomas), Transitional cell carcinomas), Sarcomas, liposarcomas (Well differentiated, Dedifferentiated, Myxoid, Round cell, Pleomorphic), Pancreatic cancers (ductal adenocarcinoma, intraductal papillary mucinous neoplasm (IPMN), acinar cell carcinoma, adenosquamous carcinoma, colloid carcinoma, giant cell tumor, hepatoid carcinoma, mucinous cystic neoplasms, pancreatoblastoma, serous cystadenoma, signet ring cell carcinoma, solid and pseudopapillary tumors, squamous cell carcinoma, and undifferentiated carcinoma, pancreatic neuroendocrine tumors (PNETs) or islet cell tumors: Insulinoma, Glucagonoma, Gastrinoma, Somatostatinoma, VIPomas, PPomas), lipomas, glioblastoma multiforme, astrocytomas, hepatocellular carcinoma, and renal cell carcinoma.

Generally, in vitro tissue and cell culture systems employ culture vessels, e.g., dishes, plates, flasks, slides, to which tissues or cells are added along with a nutrient rich medium. In certain instances, culture dishes may provide a substrate to which tissues or cells may adhere, and the medium may provide the necessary components to support and promote metabolic function of the tissues and cells added thereto. Establishing a new culture of tissue or cells requires transferring sample tissues or cells to a culture dish having an aqueous culture medium. Tissue and cell types that are not buoyant may come to rest on the surface of a culture vessel where tissue or cellular attachment to the surface occurs through a complex process commonly referred to as cellular adhesion. However, certain tissue and cell types are buoyant, and therefore, float in their culture medium rather than adhere to the surface of a culture dish. For certain cell types, failure to adhere may result in cell death.

Embodiments of the present disclosure provide systems, methods, and apparatuses for in vitro culture of buoyant tissues and cells. In particular embodiments, the systems, methods, and apparatuses described herein may be adapted to culture all tissue and cell types including but not limited to: white adipose tissue (WAT), brown adipose tissue, brain, nervous system tissue, thyroid, pancreas, spleen, cartilage, liver, kidney, and bone.

Figure 3:
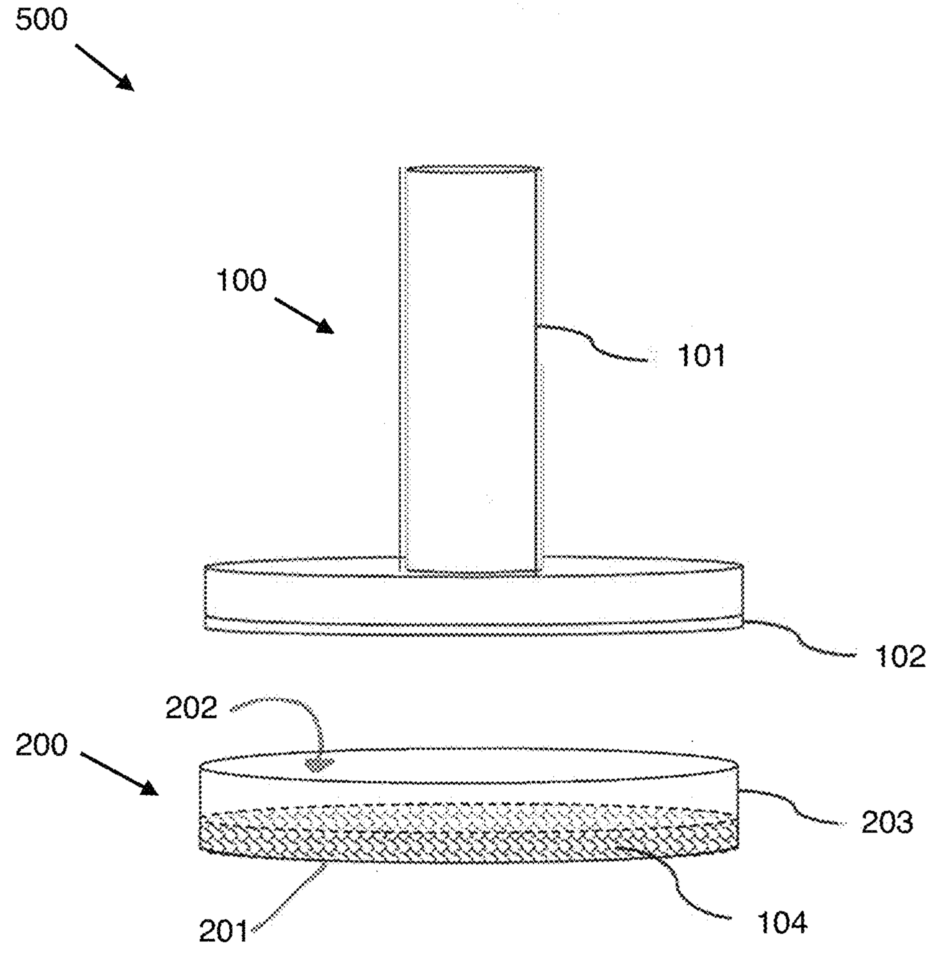
FIG. 3 is an isometric view of a culture apparatus having a layer of support cells disposed in a thermoresponsive dish and an insert device for removing the layer of support cells from the dish, according to an exemplary embodiment of the present disclosure.
Figure 4:
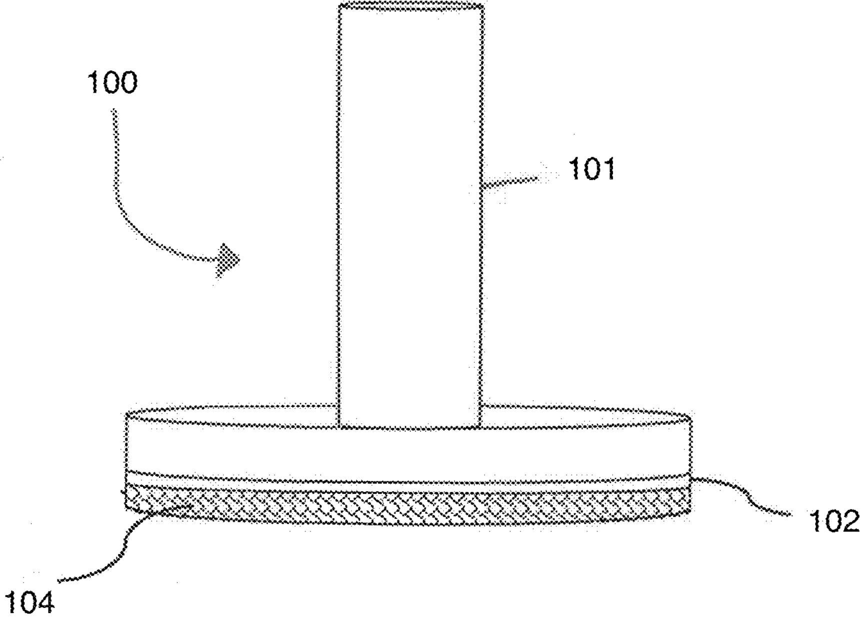
FIG. 4 is an isometric view of the insert device shown in FIG. 3 with the layer of support cells attached to a base of the insert device, according to an exemplary embodiment of the present disclosure.

Referring to FIGS. 3 to 8, different views of a system for culturing buoyant cell types is shown. FIG. 3 illustrates an exemplary embodiment of a culture apparatus 500 for culturing buoyant cell types. Culture apparatus 500 may include a culture vessel 200, e.g., a culture dish 200, and an insert 100. In certain non-limiting embodiments, the culture vessel 200 and insert 100 may comprise materials that promote adhesion of tissues or cells to the surface of the vessel or the insert.

In some embodiments, adhesion-promoting materials may be a component of the vessel 200 or insert 100, per se. In other embodiments, adhesion-promoting materials may be added to the vessel 200 and/or insert 100. In this embodiment, the respective base/surface of the vessel 200 and/or insert 100 may be coated with a matrix of proteins or extracellular material. Non-limiting examples of adhesion promoting materials include but are not limited to poly(N-isopropylacrylamide) (pNIPAAM/pNIPAm), modified methylcellulose, and thermoresponsive materials, e.g., thermoresponsive polyelectrolyte multilayer films, gelatin, collagen, hyaluronic acid, and cellulose.

In an exemplary embodiment of the present disclosure, a culture vessel 200 may include a culture dish 200 having a base 201, side walls 203, and an opening 202. Base 201 of culture dish 200 may be configured to allow culture of at least one layer of support cells. Culture dish 200 may be configured to include an opening 202 for insertion of an insert 100 device.

As shown in FIG. 3, insert 100 may include a base 102 and a handle 101. Handle 101 may be configured to allow insertion through the culture dish opening 202. Base 102 may be configured to allow culture of at least one layer of support cells 104.

In various embodiments, a thermoresponsive layer (not shown) may be added to the surface of a culture dish base 201, 401 or insert base 102 prior to culturing support cells. A layer of support cells 104 may be cultured on the surface of the thermoresponsive layer covering a culture dish base 201 or an insert surface 102. See, FIG. 3. Treatment of the culture dish 200 and the insert 100 surfaces with a thermoresponsive layer may allow transfer of an intact layer of support cells from either a culture dish 200 or the insert 100 to another culture dish or insert. See, FIG. 3, FIG. 4 and FIG. 5.

Figure 5:
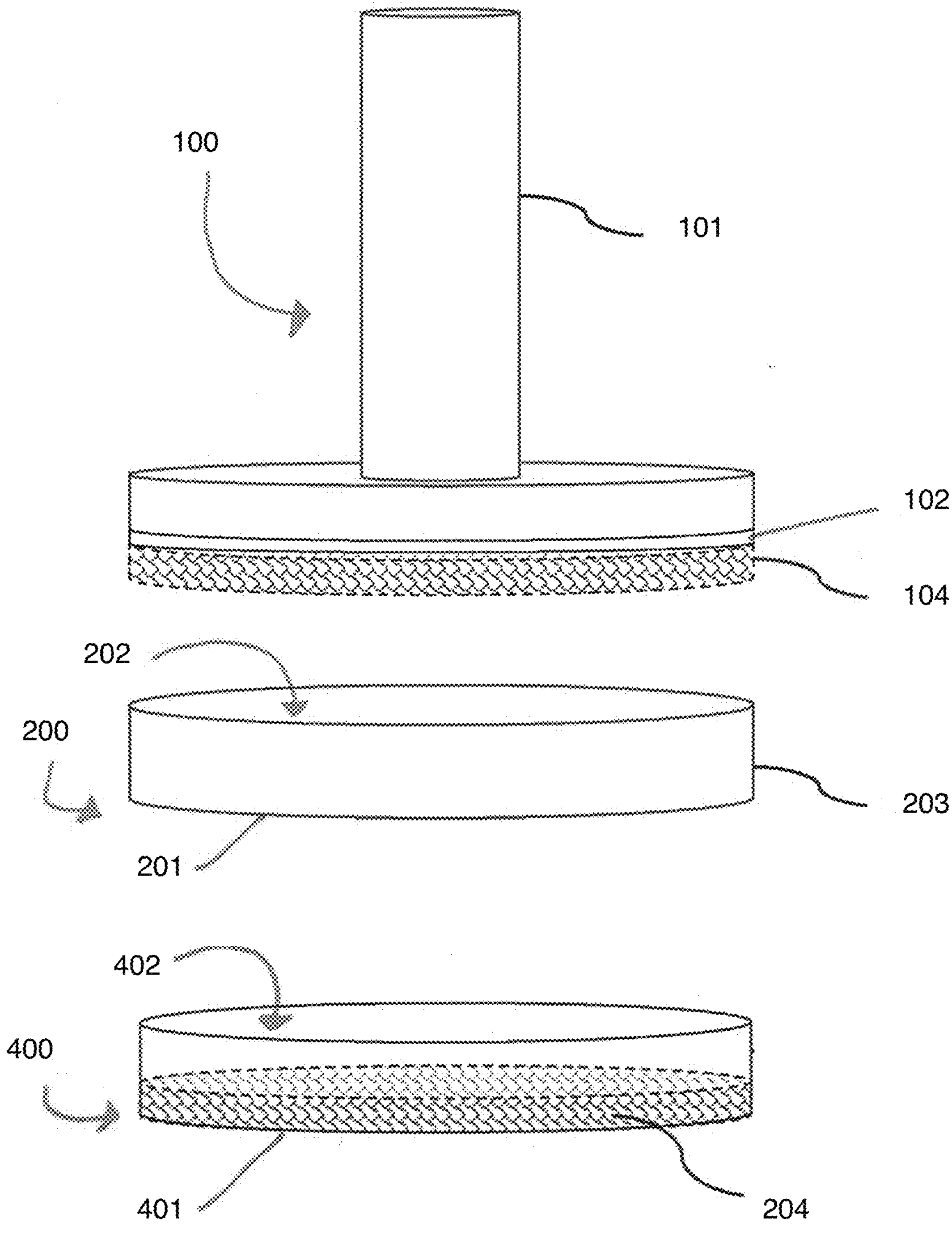
FIG. 5 is an isometric view of the culture apparatus shown in FIG. 4, with the layer of support cells attached to the base of the insert device having been removed from the thermoresponsive dish and a second culture dish containing a second layer of support cells, according to an exemplary embodiment of the present disclosure.
Figure 6:
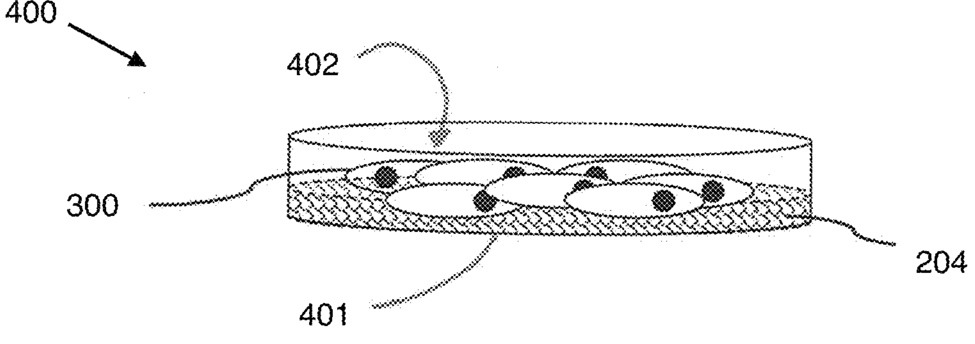
FIG. 6 is an isometric view of a culture apparatus having a buoyant cell or tissue explant deposited on a layer of support cells in a culture vessel, according to an exemplary embodiment of the present disclosure.
Figure 7:
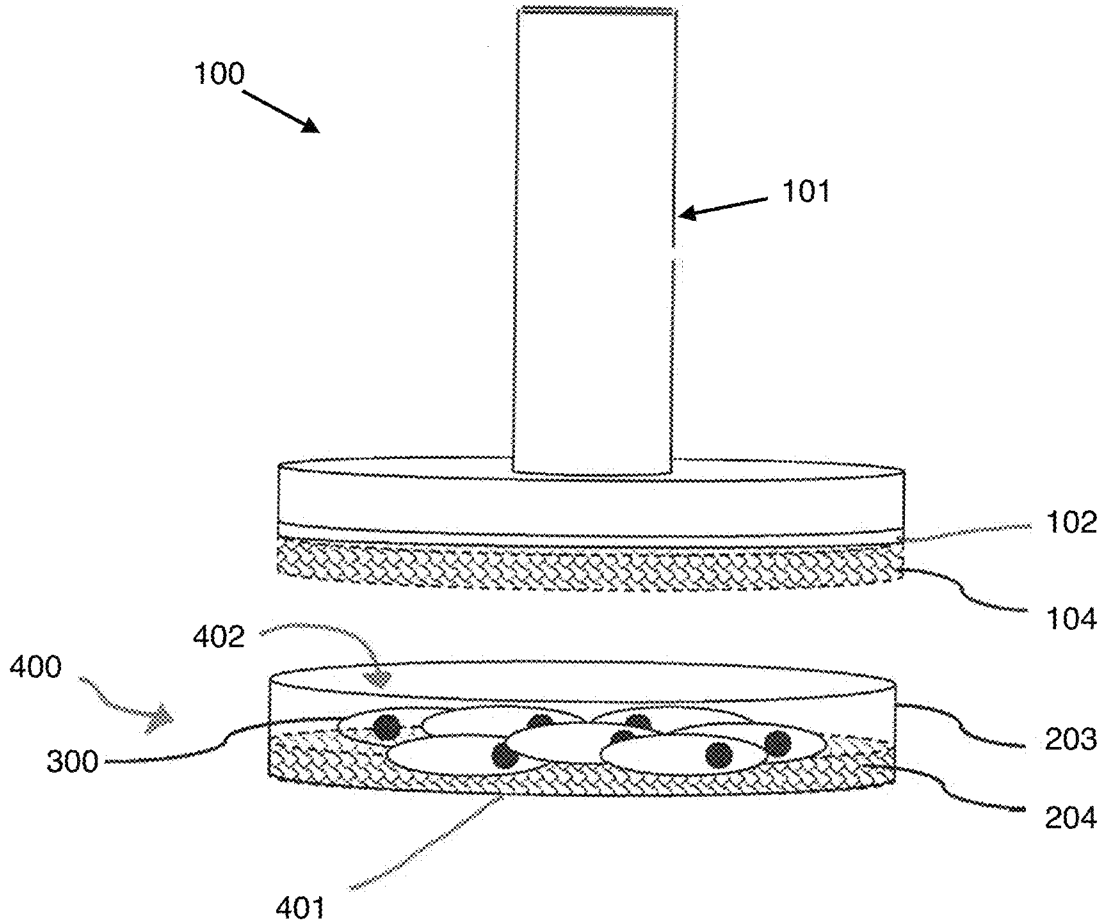
FIG. 7 is an isometric view of the culture apparatus shown in FIG. 6 and an insert device with a second layer of support cells attached to a base of the insert device to be deposited on top of the tissue explant and first layer of support cells, according to an exemplary embodiment of the present disclosure.
Figure 8:
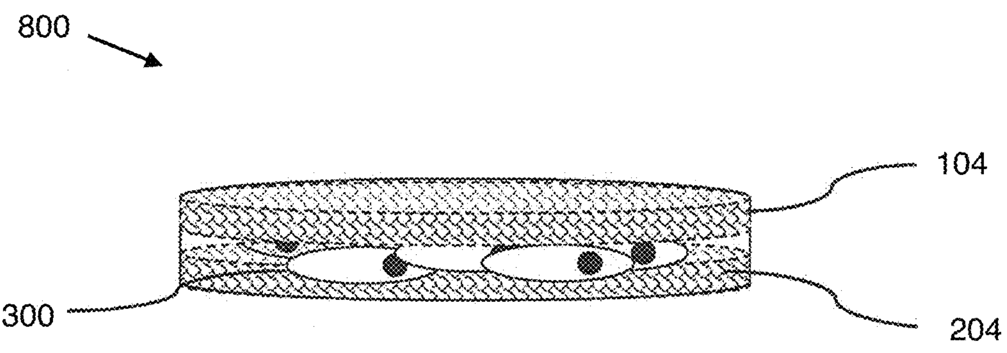
FIG. 8 is an isometric view of white adipose tissue sandwiched between two layers of support cells, according to an exemplary embodiment of the present disclosure.

In an exemplary embodiment, a first culture dish 200 having a layer of thermoresponsive material on the surface of a first culture dish base 201 may be used to culture a layer of support cells 104 that may be used to form the top layer of a sandwich construct. Insert 100 may be placed through the opening 202 of the first culture dish 200 such that the surface 102 of the insert 100 may contact the layer of support cells 104. Conditions in the culture environment may be altered to activate the thermoresponsive material, e.g., change in temperature, and release the support cell layer 104 from the first culture dish 200 base surface 201, allowing adherence of the support cell layer 104 to the surface 102 of the insert 100. See, FIG. 4. Support cells 104 having been removed from a first culture dish 200 base surface 201 by activation of a thermoresponsive material and attached to the surface 102 of the insert 100 are also shown in FIG. 5, along with a second culture dish 400 having an opening 402 and a layer of support cells 204 growing on second culture dish 400 base surface 401. In certain embodiments, the second culture dish base surface 401 may optionally be coated with a thermoresponsive material. In certain embodiments, the layer of support cells 204 may be used to form the bottom layer of a sandwich construct.

In an exemplary embodiment, subcutaneous WAT samples may be procured from human subjects during elective surgical procedures. In this embodiment, sample sizes may range from about 100 to about 5000 grams of WAT. In a particular embodiment, an experimental sample may be divided for various experimental purposes. In a particular embodiment, a portion of the subcutaneous WAT sample, e.g., 10 grams, may be minced, flash frozen, and stored as a matched primary WAT sample. In a particular embodiment, a portion of the subcutaneous WAT sample, e.g., 10 grams, may be stored in a nucleic acid lysis buffer, e.g., RNeasy Lipid Tissue Mini Kit™ (Qiagen), as a matched primary WAT sample for transcriptional confirmation. In particular embodiment, a portion of the subcutaneous WAT sample, e.g., 25 grams, may be used to produce SWAT cultures according to embodiments of the present disclosure. In a particular embodiment, a portion of the subcutaneous WAT sample, e.g., 25 grams, may be used to isolate matched support cells, e.g., adipocytes and ASCs for differentiation into diffAds using a standard protocol when the WAT is minced, enzymatically digested, and centrifuged.

In an exemplary embodiment of the present disclosure, primary WAT may be isolated from a patient and mechanically minced into segments of target tissue 300. The target tissue 300 may be human WAT. Target tissue 300 may be transferred to a culture dish 400 having a layer of support cells 204 growing on a culture dish base 401. See, FIG. 6.

Insert 100 having a layer of support cells 104 may then be inserted into culture dish 400 including target tissue 300 atop a layer of support cells 204. See, FIG. 7. In this embodiment, target tissue 300 (e.g., minced primary, human WAT) may then be sandwiched between two layers of support cells, 104, 204, to form a sandwich construct 800 (e.g., a sandwich WAT (SWAT) co-culture system). See, FIG. 8. Upper support cell layer 104 may be attached to the base 102 of insert 100 and serve to hold target tissue 300 (e.g., a buoyant tissue such as human WAT) in contact with the underlying layer of support cells 204 attached to culture dish 200 until adhesion occurs. In an exemplary embodiment, adhesion between the target tissue 300 and the layers of support cells 104, 204 occurs within minutes. In certain embodiments, the sandwich construct 800 includes two layers of support cells. In certain embodiments, the sandwich construct 800 may comprise three, four, or more layers of support cells and/or synthetic, acellular layers. In certain embodiments, a bilayer construct of the SWAT system may be entirely cellular or may contain various synthetic or acellular components.

In an exemplary embodiment, 0.5-1 mm segments of human, primary WAT are sandwiched between two layers of support cells, e.g., adipose-derived stromal cells (ADSCs), to form the SWAT co-culture system described herein. Support cells, e.g., ADSCs, may be cultured on standard tissue culture plates coated with a thermoresponsive substrate. The SWAT culture system as disclosed herein may also function using a standard culture media. Examples of standard culture media including at least low-glucose DMEM, about 10% newborn calf serum, and about 1% penicillin/streptomycin antibiotic solution.

In exemplary embodiments, the SWAT system described herein may be utilized as a test model for any extrinsic factor or system intended to modify the biology or physiology of adipose tissue or adipocytes. In various embodiments, test factors may be introduced to the cell culture medium and their impact evaluated in the isolated human adipocytes or segments of primary, human WAT. Non-limiting embodiments of test factors may include but are not limited to pharmaceutical compounds, recombinant or native viruses, recombinant or isolated nucleic acid constructs, expression vectors, siRNA construction, micro RNA constructs, genetic tools, bacteria, and environmental modulations including temperature, pressure, and modulation of gases.

As illustrated in the micrographs of FIG. 9A, a SWAT culture may be established between a bi-layer of support cells. The WAT is added to a bottom layer of unlabeled support cells and a top layer of support cells expressing enhanced green fluorescent protein (eGFP) is added. As shown in FIG. 9A, a WAT cluster of cells is sandwiched between a bi-layer of support cells, e.g., eGFP negative (bottom layer) and eGFP positive (top layer) to forming an exemplary SWAT culture system. Moreover, FIG. 9B shows microscopic images of a SWAT culture over time. The WAT cell clusters within SWAT culture are capable of retaining their morphologic stability for up to at least 47 days or about 6.7 weeks. See, FIG. 9B.

In various embodiments, the SWAT co-culture system described herein demonstrate long-term viability and stability which are important features for micro-physiologic models of terminally differentiated cells including WAT. In an exemplary embodiment of the present disclosure, long-term morphological stability is illustrated in staining of SWAT cell clusters in FIG. 10. Structural stability of the WAT cell clusters is demonstrated in FIG. 10A by restriction of neutral lipids to only WAT cells even after 51-days in SWAT culture. Likewise, propinium iodine staining of WAT cells in a SWAT culture was negative as seen in FIG. 10B. Propinium iodine negative WAT cells indicates that, after at least 18 days of SWAT culture, WAT cells were not undergoing programmed cell death, i.e., apoptosis. Finally, restriction of lipophilic staining to the adipocytes of the SWAT co-cultures further evidences the long-term viability of the systems and methods described herein. See, FIG. 10C. In contrast to conventional methods, an exemplary embodiment of the present disclosure demonstrates that the WAT cell clusters within SWAT cultures maintain their intracellular architecture, e.g., FIG. 10A, are viable and not entering a state of programmed cell death, e.g., FIG. 10B, and are maintained as separate populations.

Figure 11:
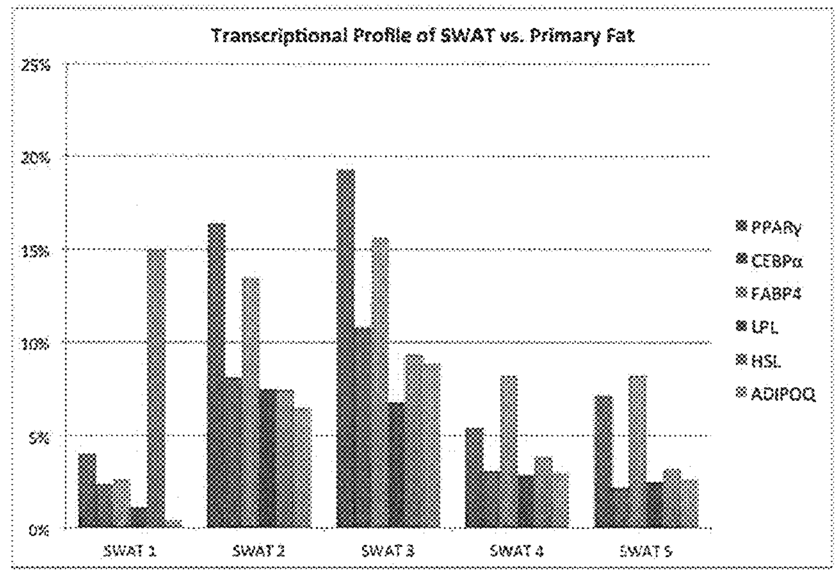
FIG. 11 is a graphical illustration showing that SWAT cultures are transcriptionally active and express genes associated with adipose tissue identity, according to an exemplary embodiment of the present disclosure.

FIG. 11 demonstrates that the SWAT system described herein is capable of maintaining a gene expression profile of at least six (6) key adipocyte identity genes including: activated receptor gamma (PPARy), which is a master regulator of adipocyte differentiation/identity; fatty acid binding protein 4 (FABP4), which is a transcription factor necessary for terminal adipocyte differentiation; CCAAT/enhancer-binding protein alpha (CEBPa), which delivers long-chain fatty acids and retinoic acid to nuclear receptors; lipoprotein lipase (LPL), which is an enzyme that hydrolyses triglycerides; hormone sensitive lipase (HSL), which hydrolyzes stored triglycerides to free fatty acids; and adiponectin (ADIPOQ), which is a central adipokine in the control of fat metabolism and insulin sensitivity. Experimentally, total RNA was collected from SWAT cultures and expression levels were compared to subject-matched primary WAT using reverse transcription polymerase chain reaction (RT-PCR). At a transcriptional level, the SWAT culture system of the present disclosure maintains the adipose tissue identity. See, FIG. 11.

At a translational level, the SWAT culture system of the present disclosure also maintains adipocyte proteins. As seen in FIG. 12, immunocytochemistry staining of SWAT cultures demonstrates the protein production of adipocyte markers including: PPARg, FABP4, beta-3 adrenergic receptor (B3-AR), which is associated with lipolysis in adipocytes, and perilipin, which is also known as protein lipid droplet-associated protein and coats lipid droplets in adipocytes.

Figure 13A:
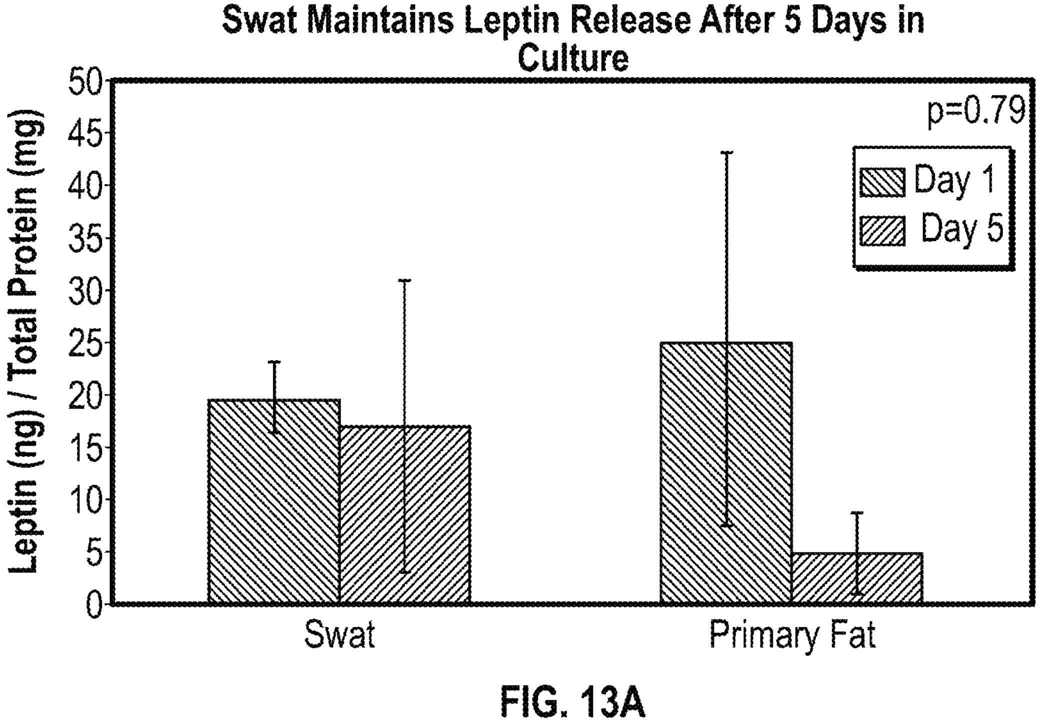
FIG. 13A is a graphical illustration showing that SWAT cultures secrete leptin at basal levels on days 1 and 5 of culture, which mirrors primary WAT, according to an exemplary embodiment of the present disclosure.
Figure 13B:
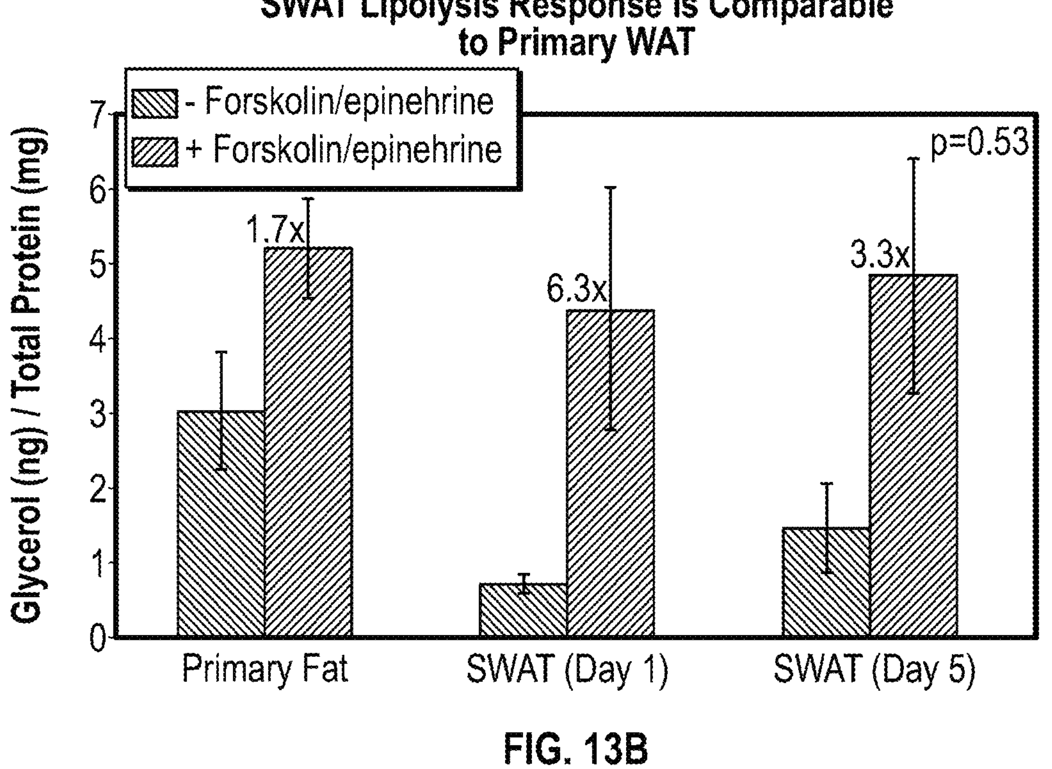
FIG. 13B is a graphical illustration showing that SWAT cultures perform lipolysis in response to catecholamine stimulation after days 1 and 5 in culture, which mirrors primary WAT, according to an exemplary embodiment of the present disclosure.
Figure 13C:
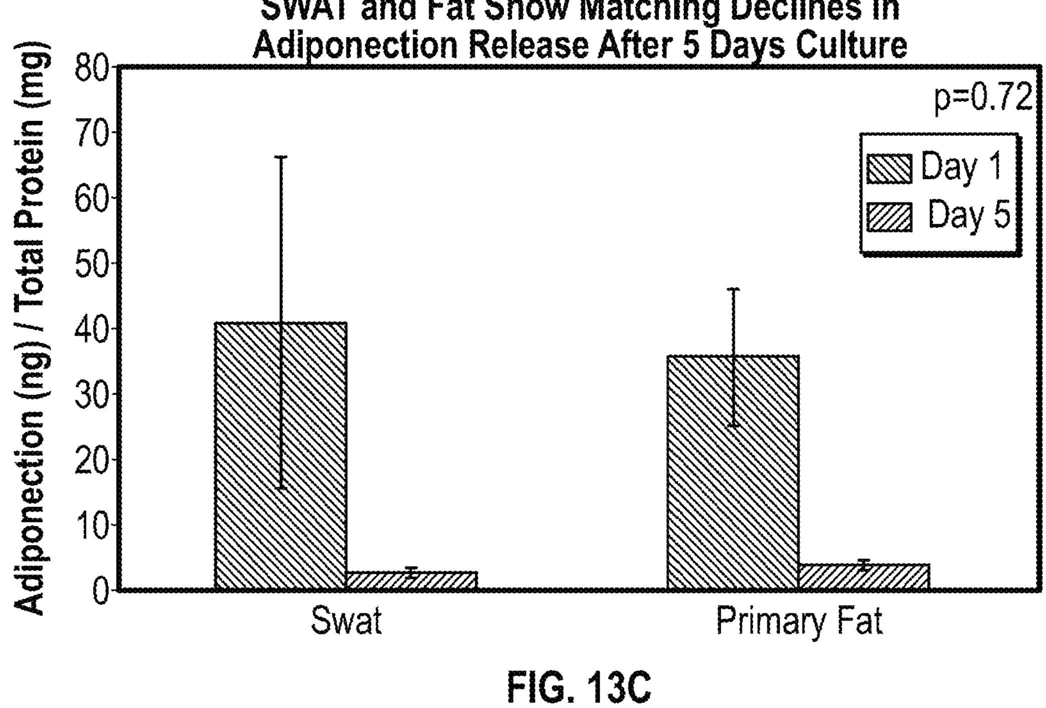
FIG. 13C is a graphical illustration showing that SWAT cultures secrete adiponectin at basal levels on days 1 and 5 of culture, which mirrors primary WAT, according to an exemplary embodiment of the present disclosure.

In addition to expressing gene and protein markers associated with adipocytes, SWAT cultures of the present disclosure also perform basal endocrine functions. In certain embodiments of the present disclosure, it may be desirable to maintain the functionality of tissues and cells in culture models as close the native tissue as possible. In various embodiments, SWAT clusters maintain their native endocrine function. Primary, human WAT is an endocrine tissue which secretes at least 2 hormones including: leptin and adiponectin. Based on normalized, quantitative ELISA assays, as illustrated in FIG. 13A and FIG. 13C, SWAT cultures secrete leptin and adiponectin at similar levels as subject-matched WAT after both one (1) and five (5) days in culture. See, FIG. 13A and FIG. 13C.

Further, the SWAT culture system described herein performed lipolysis at levels similar to primary WAT in response to exogenous signals. See, FIG. 13B. Lipolysis, which is the process of converting stored fats into metabolic fuel, is a central function of WAT. In vivo, lipolysis occurs at a basal rate and is upregulated by catecholamines. In vitro, lipolysis can be quantified by measuring the amount of free glycerol released with normalization to total protein levels using a conventional Bradford total protein assay. In a particular embodiment of the present disclosure, SWAT cultures were exposed to 100 μM forskolin+1 μM epinephrine for three (3) hours. After 1-day and 5-days in culture, SWAT cultures performed lipolysis at levels similar to primary WAT in response to stimulation.

In another exemplary embodiment, the SWAT culture system described herein may maintain native functionality after at least ten days of SWAT culture. As shown in FIG. 14, a SWAT culture was harvested after ten days of SWAT culture and subcutaneously injected into immunocompromised eGFP-labeled mice (NOD-scid IL2Rγnull). It is known that implanted tissue must recruit a new blood supply, i.e., induce vascularization, or the tissue will die, i.e., necrosis, within 48 hours and subsequently be liquefied by the host. In an exemplary embodiment, SWAT transplants were re-harvested from their mice hosts ten days after subcutaneous injection. Upon visual examination, the injected SWAT tissues were readily seen by the naked eye. See, FIG. 14 (Re-harvest). Further, histological analysis revealed that the SWAT transplants retained the architecture characteristic of WAT and did not express eGFP endogenous to the mouse host. See, FIG. 14 (SWAT and Neg). This data indicates that SWAT cultures may retain sufficient native functionality to enable SWAT tissue engraftment even after ten days in SWAT culture. Because recruitment of new, host blood supply, i.e. vascularization, is a highly complex process, this data further indicates that the SWAT system described herein may be a robust, micro-physiologic model of human WAT.

Figure 15A:
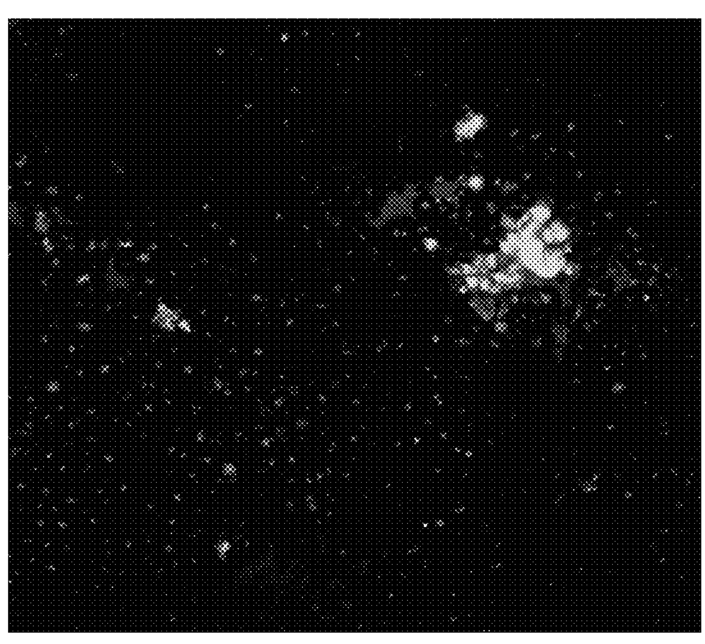
FIGS. 15A and B show images illustrating the SWAT model seeded with tumor cells, according to exemplary embodiments of the disclosure.
Figure 15B:
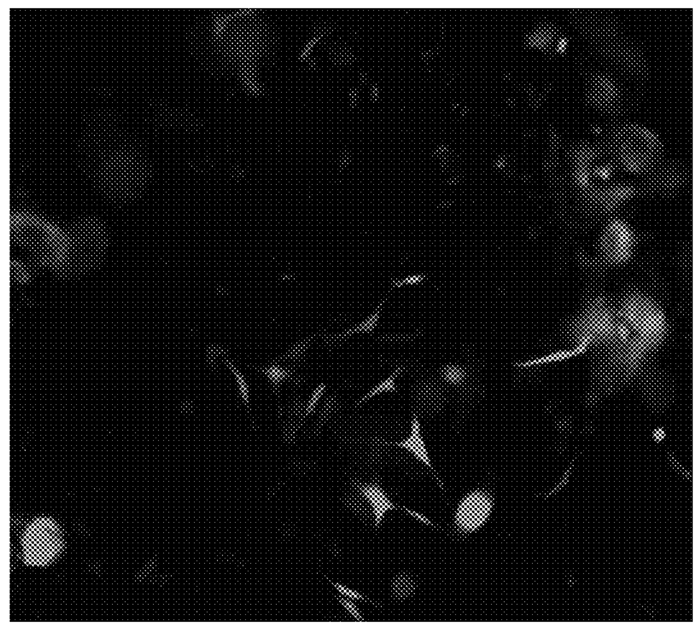

FIGS. 15A and B show images illustrating the SWAT model seeded with tumor cells. This exemplary embodiment demonstrates that breast cancer cells expressing fluorescent proteins can persist to at least 14 days in culture within human breast tissue. FIG. 15A shows a time-lapse image of luminal breast cancer cells expressing green fluorescent protein with evidence of mitosis and cancer cell motion. These cellular behaviors indicate the imaged cancerous cells were proliferating. FIG. 15B shows a time-lapse image of triple-negative breast cancer cells expressing red fluorescent protein with evidence of mitosis and cancer cell motion. These cellular behaviors indicate the imaged cancerous cells were proliferating.

Figure 17:
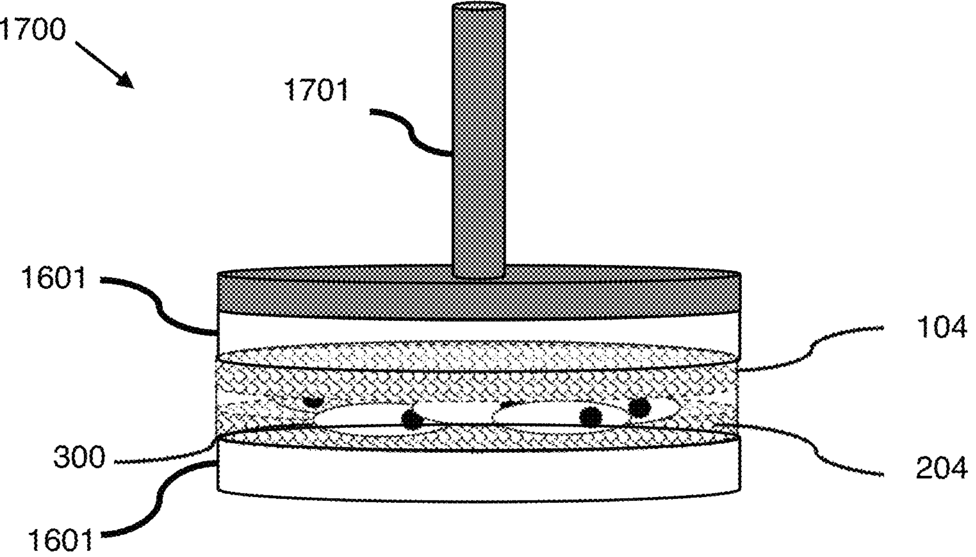
FIG. 17 is a further illustration of a means for shipping the SWAT model with a mechanical means for holding the gelatin layers in place during shipping, according to exemplary embodiments of the disclosure.

In another exemplary embodiment, a method for transporting the SWAT model is provided. FIG. 16 illustrates a system 1600 for transport of the SWAT model wherein gelatin layers 1601 may be deposited on top of and around the SWAT model. Target tissue 300 may further include other cell types including but not limited to cancer cells or tumors. A method for producing a transportable SWAT model may include generating the SWAT model on biocompatible, stable, non-reactive material on the surface of a culture vessel (e.g. dish or multi-well plate) or other substrate surface, immersing the SWAT in a biological antifreeze (e.g. Wisconsin transplant solution) to allow the temperature of the model to be brought to freezing or near freezing without the formation of ice crystals, lowering the temperature to freezing or near freezing to lower the metabolic demand of the cells, then layering gelatin on top of the complex of cells. The gelatin may be layered over the SWAT as a liquid, and the gelatin then slightly expands when transitioning from liquid to solid. This expansion when layered over the top and sides of a sandwich construct slightly compresses the sandwich construct and prevents the cells of the buoyant tissue from floating out of the construct. While gelatin layers may have been used to provide a surface for adhering cells to a culture plate, gelatin has not been used in this field to produce the compressive effect as seen while developing this shipping solution. FIG. 17 illustrates a further embodiment of the system of FIG. 16, system 1700, wherein a mechanical device 1701 may be used to hold the gelatin layers in place during transport. The mechanical device 1701 may be a plunger, a spring mechanism, a rubber gasket or another suitable device or means.

FIG. 18 is a flow chart for an exemplary process 1800 for preparing a sandwich construct for maintaining a target buoyant tissue, such as WAT. Certain steps of the process may be performed in any order. To prepare a sandwich construct, at least a top and a bottom layer of support cells must be provided. A bottom layer of support cells (e.g., support cell layer 204) may be prepared by seeding support cells in a first culture vessel (e.g., second culture dish 400), and culturing the bottom-layer support cells until they form a confluent layer on the base of the first culture vessel (1802). The bottom layer of support cells may be cultured at approximately body temperature (e.g., at a temperature between 36° C. and 38° C. for human cells, or at a warm temperature). A top layer of support cells (e.g., support cell layer 104) may be prepared by seeding support cells in a second culture vessel, where the second culture vessel may be coated with a warm-adhesion-promoting material (e.g., poly-N-isopropylacrylamide (pNIPAAm)) (1804). The top layer of support cells may be cultured at approximately body temperature until they form a confluent layer on the base of the second culture vessel, where the second culture vessel base is the same size as the first culture vessel base. In certain embodiments, where multiple sandwich constructs are desired, e.g., in a multi-well plate such as a six-well plate, the culture vessels may be individual wells of a first and second multi-well plate, and each step is performed for each respective well of the first or second plate. In certain embodiments, either layer of support cells may be grown on a substrate such as an insert device, a thermoresponsive material, an alternative growth surface, or combinations of same.

An insert device (e.g., device 100) may be prepared for transferring the top-layer cells to assemble the sandwich construct, where the insert device bears a surface that matches the size of the base of the second culture vessel, and the insert device surface is coated with a cool-adhesion-promoting material (e.g., gelatin) (1806). The insert device may be inserted into the second culture vessel, and the top layer of support cells allowed to adhere to the coated surface of the insert device at a moderate temperature such as room temperature (e.g., about 20° C.) (1808).

The second culture vessel, together with the insert device in contact with the top layer of support cells, may be cooled to a low temperature, e.g., using an ice water bath (1810). This may destabilize the warm-adhesion-promoting material and allow the top layer of cells (e.g., layer of support cells 104) to dissociate as an intact sheet from the second culture vessel base while remaining adhered to the cool-adhesion-promoting material on the insert device (see, e.g., insert device 100 as shown in FIG. 5).

Minced or lipoaspirated buoyant target tissue (e.g., target tissue 300) may be obtained and transferred into the first culture vessel (e.g., second culture dish 400) holding the bottom layer of support cells (1812).

The insert device (now carrying the top layer of support cells) may be moved to the first culture vessel holding the buoyant tissue and bottom layer of support cells to assemble a sandwich arrangement, the sandwich arrangement comprising a bi-layer of support cell layers sandwiching the buoyant tissue, and may be incubated at approximately the typical body temperature for the organism of the buoyant tissue (1814). This warm incubation temperature may promote adhesion between the bi-layer of support cell layers, while meanwhile destabilizing or melting the cool-adhesion-promoting material. The destabilization of the cool-adhesion-promoting material may allow removal of the insert while leaving the top layer of support cells adhered to the buoyant tissue and bottom layer of support cells. (In certain embodiments, any melted cool-adhesion-promoting material remaining in the first culture vessel may be removed.) The first culture vessel should now contain a complete sandwich construct comprising two support cell layers and a target tissue (e.g., sandwich construct 800).

Figure 19:
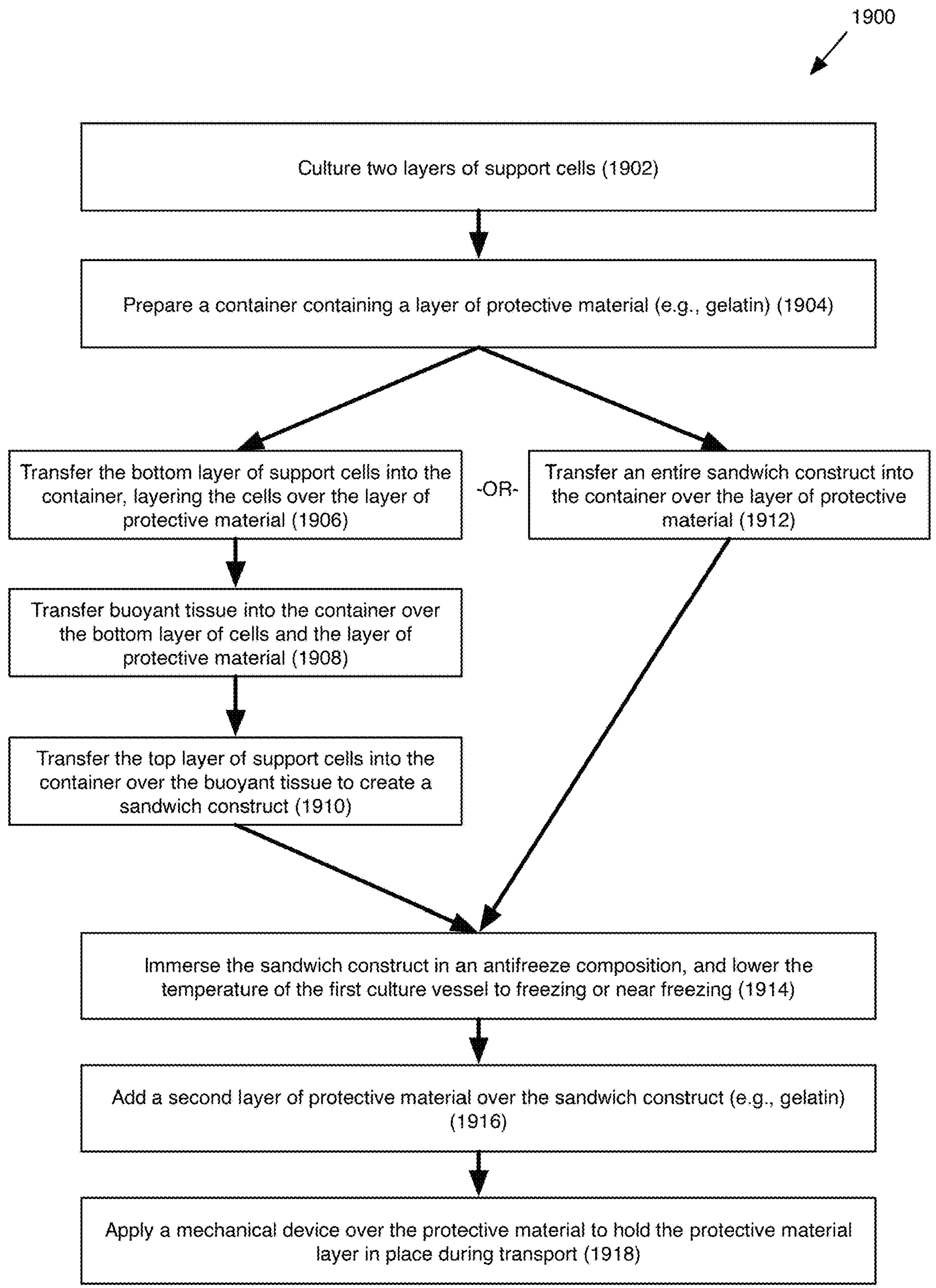
FIG. 19 is a flow chart for an exemplary process for preparing a sandwich construct containing a buoyant tissue for shipment, according to exemplary embodiments of the disclosure.

FIG. 19 is a flow chart for an exemplary process 1900 for preparing a sandwich construct containing a buoyant tissue for shipment. For each desired sandwich construct, culture a top and bottom layer of support cells (1902). For example, each layer of support cells may be cultured on a culture vessel or on the surface of an insert device. The culture vessel or insert device may have a thermoresponsive material coating or structure to facilitate transfer of the support cell layer. For each desired sandwich construct, prepare a container that may contain a layer of a protective material, such as a gelatin (1904). For example, the container may be a culture vessel such as a well of a six-well plate, or a culture plate. A first layer of support cells may be transferred into the container to form the bottom layer of the sandwich construct, layered on top of the protective material (1906). In certain embodiments, the sandwich construct is assembled/cultured directly on the base of the container, e.g., without the layer of protective material of step 1904, and, e.g., a bottom/first layer of support cells is grown on the base of the container. Buoyant tissue may be transferred into the container over the bottom layer of support cells (1908). Next, a second, top layer of support cells may be transferred into the container (i.e., over the buoyant tissue, bottom layer of support cells, and protective material) to form the sandwich construct (1910). In certain embodiments, each layer of support cells may be transferred using an insert device such as insert device 100. In certain embodiments, an entire sandwich construct may be transferred as a unit into the container containing the protective material (1912), rather than layer-by-layer as in steps 1906, 1908, and 1910. In certain embodiments, a sandwich construct may be first treated and cooled prior to being transferred as a unit into the container containing the cool-adhesion-promoting material. In certain embodiments, the sandwich construct is treated by immersing the sandwich construct in an antifreeze composition and cooled by lowering the temperature of the sandwich construct to freezing, near freezing, or below freezing (e.g., 2° C., 1° C., 0° C., or −80° C.). An antifreeze composition may be, for example, a biological antifreeze (e.g., University of Wisconsin cold storage solution), a synthetic version of a biological antifreeze, or a non-toxic composition that prevents crystal formation in aqueous solution at temperatures near and below 0° C. In certain embodiments, after step 1910 or 1912, the sandwich construct is treated and cooled (1914). A second layer of protective material, such as gelatin, may be applied to the treated sandwich construct to encapsulate the sandwich construct on all sides (1916). In certain embodiments, the sandwich construct is not treated with an antifreeze composition, and is only cooled to a refrigerator temperature such as between 0° C. and 5° C., or approximately 2° C., 3° C., or 4° C. In certain embodiments, there is no layer of protective material beneath the sandwich construct, and the sandwich construct may adhere directly to the bottom of the container. In certain embodiments, the encapsulated sandwich construct is additionally fixed in place for shipment using a mechanical device, such as mechanical device 1701 (1918). As used herein, a protective material may be a material that is stable at cool temperatures such as freezing, near freezing, or below freezing. In certain embodiments, the protective material may be a gelatin or a cryogel. In certain embodiments, the protective material slightly expands when transitioning from liquid to solid; this slight expansion when layered over the top and sides of a sandwich construct slightly compresses the sandwich construct and prevents the cells of the buoyant tissue from floating out of the construct. In certain embodiments, the protective material is also stable at room temperatures, such as 15-25° C. In certain embodiments, the protective material must have a melting point below, e.g., 30°, 40°, or 50° C. to avoid heat damage to the sandwich construct when applied as a liquid. In certain embodiments, the protective material may damp vibrations. In certain embodiments, the protective material may be a cool-adhesion-promoting material. In certain embodiments, the protective material may form a coating on the container and/or the sandwich construct.

Figure 20:
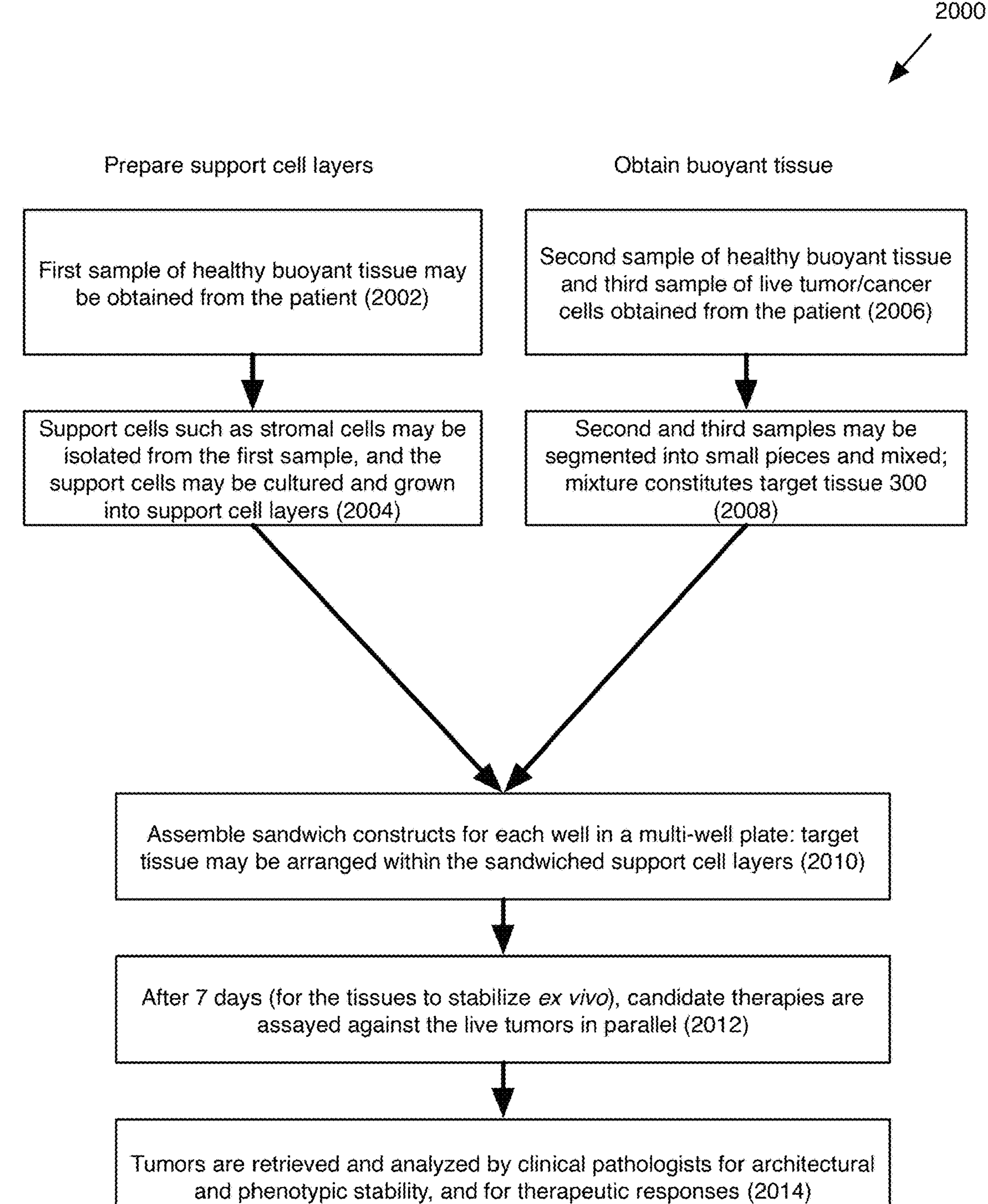
FIG. 20 is a flow chart for an exemplary process for preparing a patient-matched ex vivo model for evaluating the sensitivity of tumors to a panel of candidate therapies, according to exemplary embodiments of the disclosure.

FIG. 20 is a flow chart for an exemplary process 2000 for preparing a patient-matched ex vivo model for evaluating the sensitivity of tumors to a panel of candidate therapies. The process 2000 can be applied to tumors and other cancer cells associated with buoyant cell types such as WAT (e.g., breast cancer), prostate cancers, and other cancers referenced in this disclosure. In certain embodiments, steps of process 2000 may be performed in a different order. A sandwich construct can be prepared based on a patient's own tissue and tumor samples. The patient may be a human or another animal. In process 2000, one or more samples of a patient's healthy buoyant tissue may be obtained, and used as a source for both support cells and the target tissue of a sandwich construct. A sample of the patient's tumor or other cancer cells may be obtained and combined with a portion of the patient's healthy buoyant tissue sample(s) to serve as the target tissue 300 of the sandwich construct—i.e., the target tissue 300 may be a tissue explant. More specifically, a first sample of healthy buoyant tissue may be obtained from the patient (2002). For example, during a tumor biopsy, a separate sample of healthy buoyant tissue such as breast tissue can be obtained from the patient (e.g., 5, 10, 15, or 20 g). Support cells such as stromal cells may be isolated from the healthy buoyant tissue sample from the patient. For example, 1-5 million, or 2-3 million support cells may be isolated via mechanical and enzymatic digestion from the healthy buoyant tissue. The support cells may be cultured and grown into layers (e.g., support cell layers 104 and 205) (2004). For example, breast-derived stromal cells (BSC) may be isolated from a biopsy-associated healthy breast tissue sample and grown into BSC cell sheets.

A second sample of the patient's healthy buoyant tissue and a third sample of the live tumor/cancer cells may be obtained in order to prepare the target tissue of the sandwich construct (2006). In certain embodiments, the second buoyant tissue sample and the third tumor sample are obtained at a later date, such as weeks later, than the sample of step 2002. This elapsed time may allow time to prepare the support cell layers. In certain embodiments, the first buoyant tissue sample of step 2002 and the second buoyant tissue sample of step 2006 are obtained at the same time, and may be partitioned from the same sample. For example, at the time of tumor excision, weeks after the patient's tumor biopsy, samples of healthy human breast tissue (e.g., 5, 10, 15, or 20 g) and live tumor (1-2 g, or 1-5 g) may be obtained from the same patient. In certain embodiments, the support cell layers are alternatively derived from a cell line or a different individual's buoyant tissue sample. In certain embodiments, for an adipose tissue-associated cancer, the first sample of healthy buoyant tissue is obtained from the same adipose tissue depot as the second sample, and the first sample is taken from the same type of organism but a different individual. In certain embodiments, the second sample of healthy buoyant tissue and the third tumor sample are obtained from different individuals.

The second sample of healthy buoyant tissue and third sample of live tumor may be segmented into small pieces and mixed in preparation for serving as the target tissue of a sandwich construct (2008). For example, the two samples may be minced into small pieces approximately 0.5-1 mm in diameter. In certain embodiments, only tumor or cancer cells are included in the target tissue 300, and no second sample of buoyant tissue is mixed in. In certain embodiments, the third sample of live tumor is labeled so that the tumor material can readily be visualized and retrieved for analysis. The tumor label should be non-cytotoxic to the tumor cells. For example, the label may be CELLTRACKER™ Green CMFDA Dye (5-chloromethylfluorescein diacetate).

The mixture of buoyant tissue and tumor tissue from the second and third samples (e.g., target tissue 300) may be arranged within the sandwiched support cell layers, and may be used to populate each well in a multi-well plate with a patient-matched sandwich construct (2010). For example, human breast tissue and tumor fragments may be sandwiched between BSC cell sheets in a multi-well format. After the tissues of the sandwich constructs have stabilized, candidate therapies may be administered to the live tumors in parallel (2012). After a period of time has elapsed to allow candidate therapies to take effect, tumors may then be retrieved from the sandwich constructs and analyzed to determine the effectiveness of each candidate therapy on the patient's tumor (2014). For example, tumors may be evaluated to determine the effect on the tumor's architecture and phenotypic stability, and for therapeutic responses. For example, tumors may be evaluated for: changes in proliferation markers (e.g., changes in Ki67 expression), cell death markers (e.g., propidium iodide staining), tumor phenotype stability (e.g., by staining for hormone receptors to identify a change from HR+ to HR−), changes in tumor architecture (e.g., by staining for hematoxylin and eosin), or changes in genomic, transcriptional, proteomic, acetylation, and methylation profiles for one or more tumors in the panel of sandwich constructs.

Exemplary embodiments of the present disclosure provide a system that may allow investigation into effective anti-obesity strategies. It was previously understood that only brown adipose tissue was capable of burning energy in a process known as thermogenesis. However, in both rodents and diffAds models, it is known that white adipocytes could be induced to become thermogenic beige/"brite" adipocytes (i.e., the mixture of white and brown adipocytes referred to herein as brAds), which may be identified biochemically based on an upregulation of uncoupling protein 1 (UCP1) in response to elevated intracellular cyclic AMP (cAMP) levels. Specifically, induction of UCP1 transforms WAT into thermogenic cells and leads to an alternation in the cellular morphology.

Morphologically, brAds shift from a large, unilocular phenotype associated with WAT cells to a multilocular phenotype. The WAT-specific source of brAds has been confirmed by lineage tracing studies in rodents: brAds are myogenic factor 5 (Myf5) negative whereas brown adipocytes share a Myf5+ lineage with skeletal myocytes. In rodents, browning has been observed in most subcutaneous and visceral WAT depots. In rodent models, the weight-loss incurred by browned WAT can be profound. Accordingly, the SWAT culture system as disclosed herein may provide a micro-physiological model system for evaluating controlled browning of culturing primary, human WAT as a feasible and effective anti-obesity strategy.

Embodiments of the present disclosure provide systems and methods for investigating the biochemistry of browning pathways identified in rodent and diffAds models which may be controlled by: beta-3 adrenoreceptors (β3-ARs), cold receptors, cardiac natriuretic receptors, Janus inhibitor kinase 3 (JAK3), and Notch 1. Each of these endogenous biochemical pathways provide numerous candidate targets for pharmaceutical intervention. Several compounds have browned WAT in rodents and in diffAds. In rodents, chemical induction of browned WAT successfully ameliorated obesity and cured type 2 diabetes. Accordingly, the SWAT culture system as disclosed herein may provide a micro-physiological model system for evaluating candidate pharmaceuticals in primary, human WAT tissues.

Exemplary embodiments of the present disclosure provide an in vitro system that may allow investigation and evaluation into the effects of chemical compounds, such as pharmaceuticals, on human WAT and other buoyant cell types. Non-limiting, exemplary candidate pharmaceuticals may include but are not limited to: agonists and antagonists of beta-3 adrenoreceptors, e.g., 1&3-ARs; migrabegron, which is a 4th generation 1&3 agonist FDA-approved for use in overactive bladder syndrome, but is known to activate brown adipose tissue in humans; CL-316243, which is a specific 1&3 agonist (e.g., 1&1, 1&2, 1&3=0:1:100,000) that ameliorated obesity in obese, diabetic yellow KK mice; L-796568, which is a benzenesulfonamide-family specific 1&3 agonist, e.g., 1&1, 1&2, 1&3=1:230:660, that improved energy expenditure but did not generate notable anti-obesity effects in obese human males; BRL 26830A, which is a 1&3 agonist that demonstrated significant improvements in weight loss in a double-blinded trial.

In other exemplary embodiments, the culture system described herein may maintain native functionality of other buoyant cells in culture. Endogenous biochemical pathways may be evaluated for pharmaceutical intervention by applying and evaluating the impact of exogenous stimuli, e.g., chemical compounds. Any buoyant cell type, regardless of tissue type or species of origin, may be a candidate for use in embodiments of the present disclosure. Exemplary embodiments of buoyant tissues and cell types that may be candidates for evaluation using the apparatuses, systems and methods disclosed herein include but are not limited to: hepatocytes, renal tissue and cells, brain tissue and cells, thyroid tissue and cells, splenic tissue and cells, liver tissue and cells, central and peripheral nervous tissue and cells, and immunologic tissue and cells. Moreover, buoyant cells may be obtained from any source organism. Exemplary source organisms may include but are not limited to: plants, animals, protists, fungi, archaebacteria, and eubacteria. Additional exemplary sources of tissue or cells for evaluation using the apparatuses, systems and methods disclosed herein include but are not limited to: human, mouse, rat, monkey, dog, cat, pig, non-human primates, and fish.

Exemplary embodiments of the present disclosure provide systems and methods for investigating the biological responses of exemplary, non-limiting cell types. For example, an established buoyant tissue type may include neuronal tissue. Neuronal tissue may not readily adhere to the surface of culture dishes if, for example, excessive bubbles are introduced to an aqueous culture media. Accordingly, the buoyant tissue culture apparatuses, systems and methods disclosed herein may be directly applied to the study of neuronal tissue.

Embodiments of the present disclosure provide apparatuses, systems and methods for culturing neuronal tissue which may include embryonic or adult neuronal tissues. In an exemplary embodiment, the present disclosure provides a model system which may be used in the evaluation of neurogenesis. In other embodiments, the present disclosure may provide a system in which neuronal disease progress may be evaluated.

In an exemplary embodiment, the apparatuses, systems and methods of the present disclosure may be used to evaluate the biochemical pathways leading to the neuronal disease commonly known as Alzheimer's Disease (AD) and as well as the impact of various pharmaceutical interventions. For example, central to AD disease is the differential processing of the integral membrane protein Amyloid Precursor Protein (APP) in the normal versus disease state. In the normal state, APP is initially cleaved by α-secretase to generate sAPP and a C83 carboxy-terminal fragment. The presence of sAPP is associated with normal synaptic signaling and results in synaptic plasticity, learning and memory, emotional behaviors, and neuronal survival. In the disease state, APP is cleaved sequentially by α-secretase and γ-secretase to release an extracellular fragment called A 40/42. This neurotoxic fragment frequently aggregates and results in A 40/42 oligomerization and plaque formation. A 40/42 aggregation results in blocked ion channels, disruption of calcium homeostasis, mitochondrial oxidative stress, impaired energy metabolism and abnormal glucose regulation, and ultimately neuronal cell death. The micro-physiological system of the present disclosure provides a model for quickly and efficiently assessing buoyant neuronal tissues in vitro while maintaining the neuronal tissue in a native state.

Embodiments of the present disclosure provide apparatuses, systems and methods for evaluating the biochemical pathways involved in cardiovascular disease. Cardiovascular disease remains the leading cause of death in the United States, with over 600,000 deaths per year and annual direct costs near $300 billion. High blood pressure (HTN) and obesity are two of the most prevalent and modifiable risk factors for cardiovascular disease. HTN affects 29.1% of adult Americans and successfully treating blood pressure decreases cardiovascular disease risk by 20-50%. Obesity is more prevalent than HTN, affects 36% of adult Americans and is considered a global epidemic. However, while several classes of anti-hypertensive medications are available, no broadly effective anti-obesity medications have been approved for patient use.

In an exemplary embodiment, the apparatuses, systems and methods of the present disclosure may be used to evaluate the overlapping biochemical pathways involved in cardiovascular disease and obesity. For example, the pathogenesis of HTN often involves over-activation of the renin-angiotensin system (RAS). RAS over-activation has also been linked to obesity, a disease involving the overgrowth of WAT. Moreover, the RAS shares biochemical signaling pathways which overlap with obesity biochemical pathways as evidenced by the fact that: (i) the molecular components of RAS are present in adipose tissue, (ii) WAT secretes angiotensinogen (AGT), (iii) angiotensin II (Ang II) may induce adipogenesis in isolated adipocytes and differentiated adipocytes (diffAds), (iv) Ang II stimulation inhibited lipolysis in ex vivo human adipocytes, thus favoring adipogenesis.

Moreover, embodiments of the present disclosure confirmed that SWAT cultures are capable of maintaining RAS pathway constituent expression. For example, using RT-PCR it was determined that SWAT cultures preserves expression of key RAS components (n=5): (i) SWAT AGT expression: 62% of primary WAT (range 47-79%); SWAT ACE expression: 58% of primary WAT (range 45-71%), SWAT ATIR expression: 14% of primary; WAT (range 6-19%); SWAT AT2R expression: 231% of primary WAT (range 72-617%), SWAT Renin: no detectable expression. Further, in terms of endocrine function, SWAT secretes AGT, leptin and adiponectin as determined via enzyme-linked immunosorbent assays (ELISA). Finally, SWAT secretes 77 to 204 ng AGT per mg of total protein, and ELISA testing identified no Ang II in media from cultured SWAT. Together, this data indicates that RAS over-activation may drive adipogenesis in both systemic and autocrine fashion. In embodiments, RAS inhibition through current, approved pharmacotherapies may ameliorate both hypertension and obesity. Embodiments of the present disclosure provide apparatuses, systems, and methods for investigation into this system.

The foregoing description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. These embodiments are illustrative and the scope of the inventions is not limited to them. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein. Further still, any steps described herein may be carried out in any desired order, and any desired steps may be added or deleted.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," and the like are used merely as labels, and are not intended to impose numerical requirements on their objects.

What is claimed is:

1. A method for evaluating a candidate treatment for a breast cancer tumor in an individual, the method comprising:

isolating a population of adipose-derived stromal cells (ASCs) that form a population of support cells from a first sample of healthy breast adipose tissue;

culturing the population of support cells to form two layers of support cells;

preparing a target tissue by mixing (i) a second sample of healthy buoyant tissue, wherein the healthy buoyant tissue is breast adipose tissue that has not been digested with collagenase, and (ii) a third sample of breast cancer tumor tissue;

assembling a sandwich construct in a culture vessel and culturing the sandwich construct in the culture vessel, wherein the sandwich construct comprises a bi-layer construct in which the two layers of support cells sandwich the target tissue;

exposing the sandwich construct to the candidate treatment; and evaluating the change in the status of the breast cancer tumor tissue in the target tissue in response to the candidate treatment.

2. The method of claim 1, wherein preparing the target tissue comprises mincing the second and third samples into pieces sized 0.5 to 1.0 mm in diameter, and mixing the pieces together.

3. The method of claim 1, wherein the population of tumor tissue is labeled with a non-cytotoxic label.

4. The method of claim 1, wherein the first, second, and third samples are from the individual.

5. The method of claim 1, wherein the first sample is from a second individual.

6. The method of claim 1, wherein the candidate treatment is neoadjuvant endocrine therapy.

7. The method of claim 1, wherein the change in the status of the population of tumor tissue is a decrease in proliferation.

* * * * *